United States Patent [19]
Bourzat et al.

[11] Patent Number: 5,476,954
[45] Date of Patent: Dec. 19, 1995

[54] PROCESS FOR PREPARING TAXANE DERIVATIVES, NEW DERIVATIVES OBTAINED AND PHARMACEUTICAL COMPOSITIONS CONTAINING THEM

[75] Inventors: Jean-Dominique Bourzat, Vincennes; Alain Commercon, Vitry sur Seine; Jean-Marc Paris, Vaires sur Marne, all of France

[73] Assignee: Rhone-Poulenc Rorer S.A., Antony Cedex, France

[21] Appl. No.: 50,495

[22] PCT Filed: Nov. 22, 1991

[86] PCT No.: PCT/FR91/00928

§ 371 Date: May 21, 1993

§ 102(e) Date: May 21, 1993

[87] PCT Pub. No.: WO92/09589

PCT Pub. Date: Jun. 11, 1992

[30] Foreign Application Priority Data

Nov. 23, 1990 [FR] France ................................. 90 14635
Jul. 25, 1991 [FR] France ................................. 91 09423

[51] Int. Cl.[6] .................... C07D 305/00; A61K 31/335
[52] U.S. Cl. .................... 549/510; 549/511; 548/215
[58] Field of Search ................................. 549/510, 511; 514/449; 548/215

[56] References Cited

U.S. PATENT DOCUMENTS 4,912,039 3/1990 Riordan ..................... 435/69.1

*Primary Examiner*—C. Warren Ivy
*Assistant Examiner*—A. A. Owens
*Attorney, Agent, or Firm*—Morgan & Finnegan

[57] ABSTRACT

A method for preparing taxane derivatives having general formula (I), novel derivatives thereby obtained and compositions containing same. In general formula (I), R is t.butoxy or phenyl, $R_1$ is hydrogen or acetyl, and Ar is substituted phenyl or optionally substituted α or β-naphthyl. These novel taxane derivatives are useful as antileukemic and antitumoral agents.

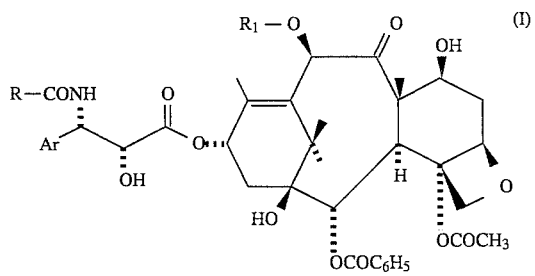

15 Claims, No Drawings

PROCESS FOR PREPARING TAXANE DERIVATIVES, NEW DERIVATIVES OBTAINED AND PHARMACEUTICAL COMPOSITIONS CONTAINING THEM

This application is a 371 of FR91100928 filed Nov. 22, 1991.

The present invention relates to a process for preparing taxane derivatives of general formula:

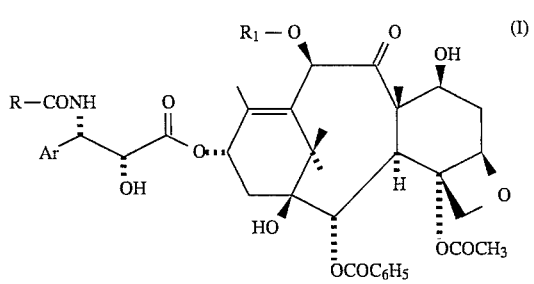

in which R represents a t-butoxy or phenyl radical, $R_1$ represents a hydrogen atom or an acetyl radical and Ar represents an aryl radical.

Preferably, Ar represents an optionally substituted phenyl or α- or β-naphthyl radical optionally substituted with one or more atoms or radicals selected from halogen (fluorine, chlorine, bromine, iodine) atoms and alkyl, aryl, arylalkyl, alkoxy, alkylthio, aryloxy, arylthio, mercapto, acylamino, aroylamino, alkoxycarbonylamino, amino, alkylamino, dialkylamino, carboxyl, alkoxycarbonyl, carbamoyl, dialkylcarbamoyl, cyano, nitro and trifluoromethyl radicals, on the understanding that the alkyl radicals and the alkyl portions of the other radicals contain 1 to 4 carbon atoms and that the aryl radicals are phenyl or α- or β-naphthyl radicals.

The present invention also relates to the new taxane derivatives of general formula (I) in which $R_1$ represents a hydrogen atom, R represents a t-butoxy or phenyl radical and Ar represents a substituted phenyl radical or an optionally substituted α- or β-naphthyl radical as stated above, that is to say the taxane derivatives of formula:

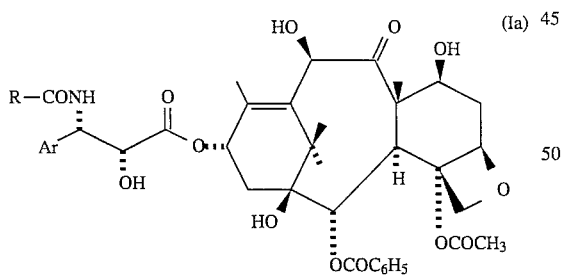

More especially, the invention relates to the new taxane derivatives of general formula (Ia) in which Ar represents a phenyl radical substituted with one or more identical or different atoms or radicals selected from halogen atoms and alkyl, alkoxy, amino, alkylamino, dialkylamino, acylamino, alkoxycarbonylamino and trifluoromethyl radicals.

Still more especially, the invention relates to the products of general formula (II [sic]) in which Ar represents a phenyl radical substituted with a chlorine or fluorine atom, or with an alkyl (methyl), alkoxy (methoxy), dialkylamino (dimethylamino), acylamino (acetylamino) or alkoxycarbonylamino (t-butoxycarbonylamino) radical.

In EP-A-0,253,739, the preparation is described of taxol from Taxotère (4-acetoxy-2-benzoyloxy-5β,20-epoxy-7β,10β-dihydroxy-9-oxo-11-taxen-13α-yl (2R,3S)-3-t-butoxycarbonylamino-3-phenyl-2-hydroxypropionate), which can itself be obtained according to the process described in EP-A-0,336,841 by condensation of 3-t-butoxycarbonylamino-3-phenyl-2-(protected hydroxy) [sic] acid with appropriately protected 10-deacetylbaccatin III. Taxol and Taxotère possess antitumour and antileukemic properties. According to Chem. Abstr. 114 94569 q (1991), taxol metabolites which are derivatives hydroxylated on the phenyl ring at the 3'-position or on the phenyl ring of the benzoyl at the 2-position are markedly less active than taxol.

According to the invention, the taxane derivatives of general formula (I) may be obtained in the following manner:

1) the oxazolidine derivative of general formula:

in which Ar is defined as above, Boc represents a t-butoxycarbonyl radical and $R_6$ and $R_7$, which may be identical or different, represent an alkyl radical containing 1 to 4 carbon atoms, optionally substituted with one or more aryl (phenyl) radicals, or an aryl (phenyl), or alternatively $R_6$ and $R_7$, together with the carbon atom to which they are linked, form a 4- to 7-membered ring, is condensed with a taxane derivative of general formula:

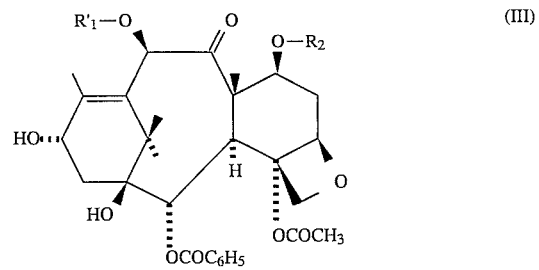

in which $R'_1$ represents an acetyl radical or a group protecting the hydroxyl function such as a 2,2,2-trichloroethoxycarbonyl radical and $R_2$ represents a group protecting the hydroxyl function such as a 2,2,2-trichloro derivative of formula (III), the condensing agent being used in a stoichiometric amount relative to the acid of formula (II) and the activating agent being used in a stoichiometric amount relative to the taxane derivative of formula (III).

The product of general formula (IV) in which $R'_1$ is defined as above and $R_2$ represents a 2,2,2-trichloroethoxycarbonyl radical may be obtained by esterification of a taxane derivative of general formula (III) in which $R'_1$ is defined as above and $R_2$ represents a trialkylsilyl radical, followed by replacement of the trialkylsilyl radical by a 2,2,2-trichloroethoxycarbonyl radical, proceeding via the intermediate product of general formula:

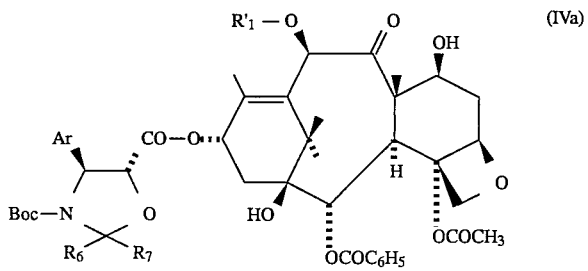

in which Ar, R'$_1$, R$_6$ and R$_7$ are defined as above.

The esterification may be performed under the conditions described above.

The product of general formula (IVa) may be obtained by treating the ester of general formula (IV) in which R$_2$ represents a trialkylsilyl radical, in which each alkyl portion contains 1 to 4 carbon atoms, with gaseous hydrochloric acid in an alcohol such as ethanol.

The product of general formula (IV) in which R$_2$ represents a 2,2,2-trichloroethoxycarbonyl radical may be obtained by treating the product of general formula (IVa) with 2,2,2-trichloroethyl chloroformate, working in a basic organic solvent such as pyridine.

2) the product of general formula (IV) in which R$_2$ represents a 2,2,2-trichloroethoxycarbonyl radical is treated with an inorganic or organic acid, where appropriate in an alcohol, under conditions which have no effect on the protective groups R'$_1$ and R$_2$, so as to obtain the product of general formula:

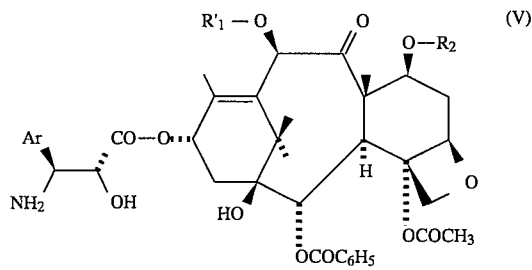

in which Ar and R'$_1$ are defined as above and R$_2$ represents a 2,2,2-trichloroethoxycarbonyl radical.

Generally, formic acid is used, where appropriate in an alcohol such as ethanol, or gaseous hydrochloric acid is used in an alcohol such as ethanol, 3) the product of general formula (V) is treated with a compound which enables a t-butoxycarbonyl or benzoyl radical to be introduced on the amino function, to obtain the product of formula:

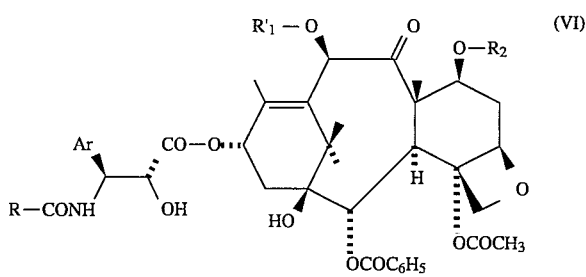

in which Ar, R and R'$_1$ are defined as above and R$_2$ represents a 2,2,2-trichloroethoxycarbonyl radical.

Generally, di-tert-butyl dicarbonate or benzoyl chloride is reacted with the product of general formula (VI), working in an organic solvent such as methylene chloride in the presence of an inorganic base such as sodium bicarbonate or an organic base such as a tertiary amine, for instance triethylamine, 4) the product of general formula (VI) is converted to a product of general formula (I) by replacement of the 2,2,2-trichloroethoxycarbonyl groups represented by R'$_1$ and R$_2$ by hydrogen atoms without affecting the remainder of the molecule.

Generally, the product of general formula (VI) is treated with zinc in the presence of acetic acid at a temperature of between 30° and 60° C., or by means of an inorganic or organic acid such as hydrochloric acid or acetic acid in solution in an aliphatic alcohol containing 1 to 3 carbon atoms in the presence of zinc.

The product of general formula (III) may be prepared under the conditions described in European Patent EP 0,336, 841.

The acid of general formula (II) may be obtained by saponification in a basic medium of the ester of general formula:

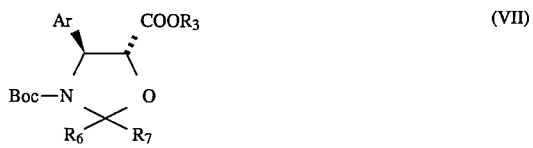

in which Ar, R$_6$ and R$_7$ are defined as above and R$_3$ represents an alkyl radical containing 1 to 4 carbon atoms, optionally substituted with a phenyl radical.

Generally, the saponification is performed by means of an inorganic base such as an alkali metal (lithium, sodium, potassium) hydroxide, or an alkali metal carbonate or bicarbonate (sodium bicarbonate, potassium carbonate or bicarbonate) in an aqueous-alcoholic medium such as a methanol/water mixture, at a temperature of between 10° and 40° C., and preferably in the region of 20° C.

The ester of general formula (VII) may be obtained by the action of a methoxyalkene optionally substituted with one or more aryl radicals (2-methoxypropene), a gem-dimethoxyalkane optionally substituted with one or more aryl radicals (2,2-dimethoxypropane) or a gem-dimethoxycycloalkane containing 4 to 7 carbon atoms, on a phenylisoserine derivative of general formula:

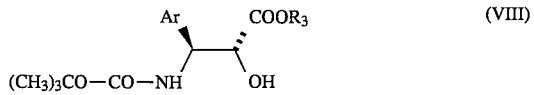

in which Ar and R$_3$ are defined as above, in racemic form or preferably in the 2R,3S form.

Generally, the reaction of the methoxyalkene or the gem-dimethoxyalkane or the gem-dimethoxycycloalkane with the product of general formula (VIII) is performed working in an inert organic solvent in the presence of a strong acid such as p-toluenesulphonic acid at a temperature between 0° C. and the boiling point of the reaction mixture. Solvents which are especially suitable are selected from aromatic hydrocarbons (benzene, toluene, xylene).

The product of general formula (VIII) may be obtained by acylation of a β-phenylisoserine derivative of general formula:

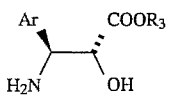 (IX)

in which Ar and $R_3$ are defined as above.

The reaction is generally performed by reacting di-tert-butyl dicarbonate, working in an inert organic solvent such as an ester, for instance methyl or ethyl acetate, at a temperature of between 0° and 40° C., and preferably in the region of 20° C.

The β-phenylisoserine derivative of general formula (IX) may be obtained by reduction of a hydroxyazide of general formula:

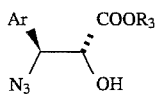 (X)

in which Ar and $R_3$ are defined as above.

Generally, the reduction is performed by means of hydrogen in the presence of a catalyst such as palladium on charcoal, working in an inert organic solvent such as ethyl acetate. It is preferable to work at a temperature of between 0° and 50° C. It is advantageous to perform the hydrogenation under a pressure of between 1 and 5 bars.

The product of general formula (X) may be obtained by the action of an alkali metal azide such as sodium azide on a β-phenylglycidic acid ester of general formula:

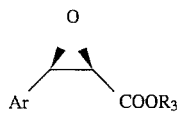 (XI)

in which Ar and $R_3$ are defined as above.

Generally, the reaction is performed in an aqueous-organic mixture such as a water/tetrahydrofuran mixture at the refluxing temperature of the reaction medium.

The ester of general formula (XI) may be obtained by dehydrohalogenation of a product of general formula:

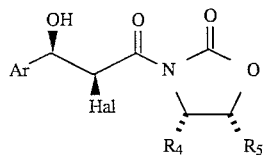 (XII)

in which Ar is defined as above, Hal represents a halogen atom, preferably a bromine atom, and $R_4$ and $R_5$, which may be identical or different, represent an alkyl radical containing 1 to 4 carbon atoms or a phenyl radical.

Generally, the reaction is performed in the presence of an excess of an alkali metal alcoholate, where appropriate prepared in situ, in an inert organic solvent such as tetrahydrofuran at a temperature of between −80° C. and +25° C.

The product of general formula (XII) may be obtained by the action of an aldehyde of general formula:

 Ar—CHO (XIII)

in which Ar is defined as above, on a halide of general formula:

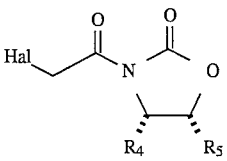 (XIV)

in which Hal, $R_4$ and $R_5$ are defined as above, anionised beforehand.

Generally, the reaction is performed in an inert organic solvent selected from ethers (ethyl ether) and halogenated aliphatic hydrocarbons (methylene chloride) at a temperature of between −80° C. and 25° C., in the presence of a tertiary amine (triethylamine) and an enolising agent (di-n-butylboron triflate).

The product of general formula (XIV) may be obtained by the action of a haloacetic acid halide, preferably bromoacetyl bromide, on the corresponding oxazolidinone.

The proton nuclear magnetic resonance spectra are performed in deuterated chloroform. Depending on the nature of the side chain, the numbering of the atoms is as follows:

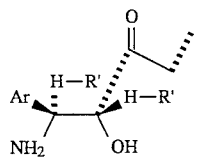

Linear chain

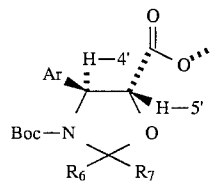

Cyclic chain

The abbreviations used have the following meanings:

s=singlet d=doublet dd=doublet of doublet t=triplet q=quartet up=unresolved peaks The examples which follow illustrate the present invention.

EXAMPLE 1

A solution of 0.5 g of 4-acetoxy-2α-benzoyloxy-5β,20-epoxy-1-hydroxy-9-oxo-7β,10-βbis[(2,2,2-trichloroethoxy-)carbonyloxy]-11-taxen-13α-yl (2R,3S)-3-tert-butoxycarbonylamino-3-(4-methylphenyl)-2-hydroxypropionate in a mixture of 10 cm³ of methanol and 10 cm³ of acetic acid is heated with stirring and under an argon atmosphere to a temperature in the region of 60° C. and then treated with 1 g of powdered zinc. The reaction mixture is then stirred for 30 minutes at 60° C., thereafter cooled to a temperature in the region of 20° C. and filtered through sintered glass lined with Celite. The sintered glass is washed with 3 times 10 cm³ of dichloromethane and the filtrates are combined and then concentrated to dryness under reduced pressure (2.7 kPa) at a temperature in the region of 40° C.

The residue is treated with 20 cm³ of distilled water and the crystallized solid is separated by filtration, washed with 4 times 5 cm³ of distilled water and dried under reduced pressure (0.27 kPa) at 20° C. for 16 hours. 0.25 g of a white meringue-like product is obtained, which product is purified by chromatography on 40 g of silica (0.063–0.2 mm) contained in a column 2 cm in diameter [eluent: dichloromethane/methanol (97:3 by volume)], collecting 20-cm³ fractions. Fractions 5 to 12 are combined and concentrated to dryness under reduced pressure (0.27 kPa) at 40° C. for 16 hours. 0.2 g of 4-acetoxy-2 α-benzoyloxy-5β, 20-epoxy-1,7β,10β-trihydroxy-9-oxo-11 -taxen-13α-yl (2R, 3S)-3-tert-butoxy-carbonylamino-3-(4-methylphenyl)-2-hydroxypropionate is thereby obtained in the form of a white meringue-like product, the characteristics of which are as follows:

rotatory power: $[\alpha]_D^{20} = -32°$ (c=0.1; methanol)

NMR spectrum (250 MHz; CDCl₃) δ (ppm): 1.14 (s, 3H: —C$\underline{H}_3$ 16 or 17); 1.24 (s, 3H: —C$\underline{H}_3$ 16 or 17); 1.35 (s,9H: —C(C$\underline{H}_3$)₃); 1.7 (s, 1H: —O$\underline{H}$ 1); 1.77 (s, 3H: —C$\underline{H}_3$ 19); 1.85 (up, 1H: —(CH)—$\underline{H}$ 6); 1.87 (s, 3H: —C$\underline{H}_3$ 18); 2.26 (up, 2H: —C$\underline{H}_2$— 14); 2.33 (s, 3H: —COC$\underline{H}_3$); 2.4 (s, 3H: C$\underline{H}_3$— C₆H₄); 2.6 (ddd, 1H, J=6.5, 9.5 and 15 Hz: —(CH)—$\underline{H}$ 6); 3.38 (d, 1H, J=5.5 Hz: —O$\underline{H}$ 2'); 3.92 (d, 1H, J=7 Hz: —$\underline{H}$ 3); 4.18 (d, 1H, J=8 Hz: —(CH)—$\underline{H}$ 20); 4.22 (up, 2H: —$\underline{H}$ 7 and —O$\underline{H}$ 10); 4.33 (d, 1H, J=8 Hz: —(CH)—$\underline{H}$ 20); 4.6 (up, 1H: —$\underline{H}$ 2'); 4.96 (dd, 1H, J=1.5 and 9.5 Hz: —Hz; —5); 5.22 (s, 1H: —$\underline{H}$ 10); 5.22 (up, 1H: —$\underline{H}$ 3'); 5.4 (d, 1H, J=9 Hz: —NHCO—); 5.68 (d, 1H, J=7 Hz: —$\underline{H}$ 2); 6.2 (t, 1H, J=9 Hz: —$\underline{H}$ 13); 7.23 (AB, 4H, $J_{AB}$=8 Hz: CH₃—C₆$\underline{H}_4$); 7.5 [t, 2H, J=7.5 Hz: —OCOC₆H₅(—$\underline{H}$ 3 and —$\underline{H}$ 5]; 7.62 [tt, 1H, J=1 and 7.5 Hz: —OCOC₆H₅(—$\underline{H}$ 4)]; 8.12 [d, 2H, J=7.5 Hz: —OCOC₆H₅(—$\underline{H}$ 2 and —$\underline{H}$ 6)].

4-Acetoxy-2α-benzoyloxy-5β,20-epoxy-1 -hydroxy-9-oxo-7β,10β-bis[(2,2,2-trichloroethoxy)carbonyloxy]-11-taxen-13α-yl (2R,3S)-3-tert-butoxycarbonylamino-3-(4-methylphenyl)-2-hydroxypropionate may be prepared in the following manner:

0.037 g of sodium hydrogen carbonate is added to a solution, maintained under an argon atmosphere, of 0.45 g of 4-acetoxy-2α-benzoyloxy-5β,20-epoxy-1 -hydroxy-9-oxo-7β,10β-bis[(2,2,2-trichloroethoxy)carbonyloxy]-11-taxen-13α-yl (2R,3S)-3-amino-2-hydroxy-3-(4-methyl-phenyl)propionate in 5 cm³ of dichloromethane, and a solution of 0.108 g of di-tertbutyl dicarbonate in 5 cm³ of dichloromethane is then added dropwise at a temperature in the region of 20° C. The solution obtained is stirred for 24 hours at a temperature in the region of 20° C. and then treated with a mixture of 15 cm³ of distilled water and 20 cm³ of dichloromethane. The aqueous phase is separated after settling has taken place and then reextracted with 20 cm³ of dichloromethane. The organic phases are combined, dried over magnesium sulphate, filtered and concentrated to dryness under reduced pressure (2.7 kPa) at 40° C. 0.5 g of 4-acetoxy-2α-benzoyloxy- 5β,20-epoxy-1-hydroxy-9-oxo-7β,10β-bis[(2,2,2-trichloroethoxy)carbonyloxy]-11-taxen-13α-yl (2R,3S)-3-tert-butoxycarbonylamino-3-(4-methylphenyl)-2 -hydroxypropionate is thereby obtained in the form of a white meringue-like product.

4-Acetoxy-2α-benzoyloxy-5β,20-epoxy-1 -hydroxy-9-oxo-7β,10β-bis[(2,2,2-trichloroethoxy)carbonyloxy]-11-taxen-13α-yl (2R,3S)-3-amino-2-hydroxy-3-(4-methylphenyl)propionate may be prepared in the following manner:

A solution of 0.6 g of 4-acetoxy-2α -benzoyloxy-5β,20-epoxy-1-hydroxy-9-oxo-7β,10β-bis[(2,2,2-trichloroethoxy)carbonyloxy]-11-taxen-13α-yl (4S,5R)-3-tert-butoxycarbonyl-2,2-dimethyl-4-(4 -methylphenyl)-5-oxazolidinecarboxylate in 6 cm³ of formic acid is stirred for 4 hours at a temperature in the region of 20° C. and then concentrated to dryness under reduced pressure (2.7 kPa) at 40° C. The residue is treated with 40 cm³ of toluene and the solution obtained is then concentrated to dryness under reduced pressure (2.7 kPa) at 40° C. The same operation is repeated with 40 cm³ of toluene. The meringue-like product obtained is dissolved in 50 cm³ of dichloromethane and the solution obtained is treated with 25 cm³ of saturated aqueous sodium hydrogen carbonate solution. The aqueous phase is separated after settling has taken place and reextracted with 25 cm³ of dichloromethane. The organic phases are combined, dried over magnesium sulphate, filtered and then concentrated to dryness under reduced pressure (2.7 kPa) at 40° C. 0.65 g of a white meringue-like product is obtained, which product is purified by chromatography on 40 g of silica (0.063–0.2 mm) contained in a column 2 cm in diameter [eluent: dichloromethane/methanol (98:2 by volume)], collecting 20-cm³ fractions. Fractions 5 to 9 are combined and concentrated to dryness under reduced pressure (2.7 kPa) at a temperature in the region of 40° C. 0.45 g of 4-acetoxy-2α-benzoyloxy-5β,20-epoxy-1 -hydroxy-9-oxo-7β,10β-bis[(2,2,2-trichloroethoxy)carbonyloxy]-11-taxen-13α-yl (2R,3S)-3-amino-2-hydroxy-3-(4-methyl-phenyl)propionate is thereby obtained in the form of a white meringue-like product.

4-Acetoxy-2α-benzoyloxy-5β,20-epoxy-1 -hydroxy-9-oxo-7β,10β-bis[(2,2,2-trichloroethoxy)carbonyloxy]-11-taxen-13α-yl (4S,5R)-3-tert-butoxycarbonyl- 2,2-dimethyl-4-(4-methylphenyl)-5-oxazolidinecarboxylate may be prepared in the following manner:

0.247 g of N,N'-dicyclohexylcarbodiimide, 4-acetoxy-2α-benzoyloxy-5β,20-epoxy-1,13α-dihydroxy-9 -oxo-7β,10β-bis[(2,2,2-trichloroethoxy)carbonyloxy] -11-taxene and 0.046 g of 4-(dimethylamino)pyridine are added to a solution of 0.4 g of (4S,5R)-3 -tert-butoxycarbonyl-2,2-dimethyl-4-(4-methylphenyl)-5-oxazolidinecarboxylic acid in 10 cm³ of toluene. The reaction medium is then heated with stirring for 3 hours to a temperature in the region of 80° C., thereafter cooled to a temperature in the region of 20° C. and treated with a mixture of 20 cm³ of dichloromethane and 25 cm³ of saturated aqueous sodium hydrogen carbonate solution. The aqueous phase is separated after settling has taken place and then reextracted with 15 cm³ of dichloromethane. The organic phases are combined, dried over magnesium sulphate, filtered and then concentrated to dryness under reduced pressure (2.7 kPa) at 50° C. 1.1 g of a yellow meringue-like product is obtained, which product is purified by chromatography on 40 g of silica (0.063–0.2 mm) contained in a column 2 cm in diameter [eluent: dichloromethane/methanol (98:2 by volume)], collecting 15-cm³ fractions. Fractions 3 to 6 are combined and concentrated to dryness under reduced pressure (2.7 kPa) at a temperature in the region of 40° C. 0.6 g of 4-acetoxy-2α-benzoyloxy-5β,20-epoxy-1-hydroxy-9-oxo-7β,10β-bis [(2,2,2-trichloroethoxy)carbonyloxy]-11 -taxen-13α-yl (4S, 5R)-3-tert-butoxycarbonyl-2,2-di-methyl- 4-(4-methylphenyl)-5-oxazolidinecarboxylate is thereby obtained in the form of a white meringue-like product.

4-Acetoxy-2α-benzoyloxy-5β,20-epoxy-1,13α-dihydroxy-9-oxo-7β,10β-bis[(2,2,2-trichloroethoxy)carbonyloxy]-11-taxene may be prepared according to the method described in European Patent EP 0,336,841.

(4S,5R)-3-tert-butoxycarbonyl-2,2-dimethyl-4 -(4-methylphenyl)-5-oxazolidinecarboxylic acid may be prepared in the following manner:

A solution of 0.19 g of lithium hydroxide hydrate in 3 cm³ of distilled water is added at a temperature in the region of 25° C. to a solution of 0.54 g of ethyl (4S,5R)-3-tert-butoxycarbonyl-2,2 -dimethyl-4-(4-methylphenyl)-5-oxazolidinecarboxylate in 10 cm³ of ethanol. The reaction medium is stirred for 20 minutes at a temperature in the region of 25° C. and then concentrated to dryness under reduced pressure (2.7 kPa) at a temperature in the region of 40° C. The residue obtained is dissolved in 3.5 cm³ of distilled water and then extracted with 2 times 1 cm³ of diisopropyl ether. The aqueous phase is then acidified to a pH in the region of 1 with 5 cm³ of 1N aqueous hydrochloric acid solution and thereafter extracted with 3 times 4 cm³ of dichloromethane. The organic phases are combined, dried over magnesium sulphate, filtered and then concentrated to dryness under reduced pressure (2.7 kPa) at a temperature in the region of 40° C. 0.43 g of (4S,5R)-3-tert-butoxycarbonyl-2,2-dimethyl-4-(4-methylphenyl)-5-oxazolidinecarboxylic acid is thereby obtained in the form of an orange-colored oil.

Ethyl (4S,5R)-3-tert-butoxycarbonyl-2,2 -dimethyl-4-(4-methylphenyl)-5-oxazolidinecarboxylate may be prepared in the following manner:

A solution of 0.63 g of ethyl (2R,3S)-3-tert-butoxycarbonylamino- 2-hydroxy-3-(4-methylphenyl)propionate, 0.2 cm³ of 2-methoxypropene and 3.4 mg of pyridinium p-toluenesulphonate in 18 cm³ of toluene is stirred for 2 hours 30 minutes at a temperature in the region of 20° C. The reaction mixture is heated to boiling and the distillate is collected in a graduated vessel while a solution of 1.25 cm³ of 2-methoxypropene in 15 cm³ of toluene is added dropwise to the reaction medium so as to keep the volume of this medium constant. After 15 minutes' distillation, 3.4 mg of pyridinium p-toluenesulphonate are added and distillation is then continued for 15 minutes. The volume of distillate collected is then 20 cm³. The reaction medium is cooled to a temperature in the region of 20° C. and 2 cm³ of saturated aqueous sodium hydrogen carbonate solution are then added. The aqueous phase is separated after settling has taken place and then extracted with 2 times 5 cm³ of dichloromethane. The organic phases are combined, dried over magnesium sulphate, filtered and concentrated to dryness under reduced pressure (2.3 kPa) at a temperature in the region of 40° C. 0.54 g of ethyl (4S,5R)-3-tert-butoxycarbonyl- 2,2-dimethyl-4-(4-methylphenhyl)-5 -oxazolidinecarboxylate is thereby obtained in the form of a yellow oil.

Ethyl (2R,3S)-3-tert-butoxycarbonylamino-2 -hydroxy-3-(4-methylphenyl)propionate may be prepared in the following manner:

0.33 g of sodium hydrogen carbonate is added to a solution, maintained under an argon atmosphere, of 0.8 g of ethyl (2R,3S)-3-amino-2-hydroxy-3-(4-methylphenyl)propionate in 12 cm³ of dichloromethane, and a solution of 0.94 g of di-tert-butyl dicarbonate in 4 cm³ of dichloromethane is then added dropwise at a temperature in the region of 20° C. The solution obtained is stirred for 2 hours 30 minutes at a temperature in the region of 20° C. and then treated with 20 cm³ of distilled water. The aqueous phase is separated after settling has taken place and then reextracted with 20 cm³ of dichloromethane. The organic phases are combined, dried over magnesium sulphate, filtered and then concentrated to dryness under reduced pressure (2.7 kPa) at 40° C. After crystallization in cyclohexane, 0.65 g of ethyl (2R,3S)-3-tert-butoxycarbonylamino- 2-hydroxy-3-(4-methylphenyl)propionate, melting point 130° C., is thereby obtained.

Ethyl (2R,3S)-3-amino-2-hydroxy-3-(4-methylphenyl)propionate may be prepared in the following manner:

0.115 g of carbon powder carrying 10% of palladium is added to a solution of 1.15 g of ethyl (2R,3S)-3-azido-2-hydroxy-3-(4-methylphenyl)propionate in 35 cm³ of ethyl acetate. The reaction mixture is stirred under a hydrogen pressure of 120 kPa and at a temperature in the region of 22° C. for 8 hours and then filtered through sintered glass lined with Celite. The sintered glass is washed with 5 cm³ of ethyl acetate and the filtrates are combined and then concentrated to dryness under reduced pressure (2.7 kPa) at a temperature in the region of 40° C. 0.83 g of ethyl (2R,3S)-3-amino-2-hydroxy-3-(4-methylphenyl)propionate is thereby obtained in the form of a pale yellow paste.

Ethyl (2R,3S)-3-azido-2-hydroxy-3-(4-methylphenyl)propionate may be prepared in the following manner:

1.04 g of sodium azide and 0.86 g of ammonium chloride are added to a solution of 2.2 g of ethyl (2R,3R)-3-(4-methylphenyl)-2-oxiranecarboxylate in 60 cm³ of ethanol. The reaction mixture is stirred under reflux for 5 hours 30 minutes, then cooled to a temperature in the region of 20° C. and treated with a mixture of 50 cm³ of ethyl acetate and 50 cm³ of distilled water. The aqueous phase is separated after settling has taken place and reextracted with 50 cm³ of ethyl acetate. The organic phases are combined, dried over magnesium sulphate, filtered and then concentrated to dryness under reduced pressure (2.7 kPa) at 40° C. 2.4 g of an orange-colored oil are obtained, which product is purified by chromatography on 80 g of silica (0.063–0.2 mm) contained in a column 2 cm in diameter [eluent: cyclohexane/ethyl acetate (90:10 by volume)], collecting 50-cm³ fractions. Fractions 8 to 16 are combined and concentrated to dryness under reduced pressure (2.7 kPa) at a temperature in the region of 40° C. 1.55 g of ethyl (2R,3S)-3-azido-2-hydroxy-3-(4-methylphenyl)propionate is thereby obtained in the form of an orange-colored oil.

Ethyl (2R,3R)-3-(4-methylphenyl)-2-oxiranecarboxylate may be prepared in the following manner:

While the temperature is maintained at −75° C., 25 cm³ of a 1.6M solution of n-butyllithium in hexane are added to a solution, cooled to a temperature in the region of −75° C., 2.3 cm³ of ethanol in 40 cm³ of tetrahydrofuran, and a solution of 8.36 g of (4S,5R)-3-[(2S,3R)-2-bromo-3-hydroxy-3-(4-methylphenyl)-1 -oxopropyl]-4-methyl-5-phenyl-2-oxazolidinone in 120 cm³ of tetrahydrofuran is then added dropwise. The reaction medium is warmed to a temperature in the region of 0° C., then maintained at 0° C. for 1 hour and cooled again to a temperature in the region of −75° C. A solution of 5.04 g of citric acid in 28 cm³ of tetrahydrofuran is then added while the temperature is maintained at −75° C. The reaction medium is warmed to a temperature in the region of 15° C., then maintained at 15° C. for 1 hour and treated with a mixture of 40 cm³ of distilled water and 200 cm³ of diethyl ether. The aqueous phase is separated after settling has taken place and reextracted with 2 times 50 cm³ of diethyl ether. The organic phases are combined, dried over magnesium sulphate, filtered and then concentrated to dryness under reduced pressure (2.7 kPa) at 40° C. 5.3 g of an orange-colored oil are obtained, which product is purified by chromatography on 200 g of silica (0.063– 0.2 mm) contained in a column 2 cm in diameter [eluent: cyclohexane/ethyl acetate (90:10 by volume)], collecting 50-cm³ fractions. Fractions 10 to 20 are combined and concentrated to dryness under reduced pressure (2.7 kPa) at a temperature in the region of 40° C. After crystallization in diisopropyl ether, 2.2 g of ethyl (2R,3R)-3-(4-methylphenyl)-2-oxiranecarboxylate, melting point 66° C., are thereby obtained.

(4S,5R)-3-[(2S,3R)-2-Bromo-3-hydroxy-3-(4-methylphenyl)-1-oxopropyl]-4-methyl-5-phenyl-2-oxazolidinone may be prepared in the following manner:

23.4 cm³ of triethylamine are added at a temperature in the region of 20° C. to a solution of 35.8 g of (4S,5R)-3-(2-bromo-1-oxoethyl)-4-methyl-5-phenyl-2-oxazolidinone in 300 cm³ of anhydrous diethyl ether, and 135 cm³ of a 1M solution of di-n-butylboron triflate in dichloromethane are then added dropwise. The reaction medium is cooled to a temperature in the region of −75° C., 10.64 cm³ of 4-methylbenzaldehyde are then added while the temperature is maintained at −75° C. and the reaction medium is warmed to a temperature in the region of 20° C. and maintained at 20° C. for 18 hours. 100 cm³ of saturated sodium hydrogen sulphate solution are then added and the aqueous phase is separated after settling has taken place and reextracted with 2 times 100 cm³ of diethyl ether. The organic phases are combined, dried over magnesium sulphate, filtered and then concentrated to dryness under reduced pressure (2.7 kPa) at 40° C. 69 g of a brown oil are obtained, which product is purified by chromatography on 2,000 g of silica (0,063–0.2 mm) contained in a column 5 cm in diameter [eluent: cyclohexane/ethyl acetate (70:30 by volume)], collecting 200-cm³ fractions. Fractions 16 to 24 are combined and concentrated to dryness under reduced pressure (2.7 kPa) at a temperature in the region of 40° C. After crystallization in diisopropyl ether, 17 g of (4S,5R)-3-[(2S,3R)-2-bromo-3-hydroxy-3-(4-methyl-phenyl)-1-oxopropyl]-4-methyl-5-phenyl-2-oxazolidinone, melting point 139° C., are thereby obtained.

(4S,5R)-3-(2-Bromo-1-oxoethyl)-4-methyl-5-phenyl-2-oxazolidinone may be prepared in the following manner:

While the temperature is maintained at −75° C., 375 cm³ of a 1.6M solution of n-butyllithium in hexane are added to a solution, cooled to a temperature in the region of −75° C., of 106.2 g of (4S,5R)-4-methyl-5-phenyl-2-oxazolidinone in 1080 cm³ of anhydrous tetrahydrofuran, and 62.6 cm³ of bromoacetyl bromide are then added dropwise. The reaction medium is stirred at a temperature in the region of −70° C. for 1 hour 30 minutes, and it is then warmed to a temperature in the region of −10° C. and treated with 600 cm³ of

EXAMPLE 2

Using the procedure described in Example 1, but starting with 4-acetoxy-2α-benzoyloxy-5β,20-epoxy-1-hydroxy-9-oxo-7β,10β-bis[(2,2,2-trichloroethoxy)carbonyloxy]-11-taxen-13α-yl (2R,3S)-3-tert-butoxycarbonylamino-3-(2-fluorophenyl)-2-hydroxypropionate, 0.17 g of 4-acetoxy-2α-benzoyloxy-5β,20-epoxy-1,7β,10β-trihydroxy-9-oxo-11-taxen-13α-yl (2R,3S)-3-tertbutoxycarbonylamino-3-(2-fluorophenyl)-2-hydroxypropionate is obtained in the form of a white meringue-like product, the characteristics of which are as follows:

rotatory power: $[\alpha]_D^{20}=-42°$ (c=0.58; methanol)

NMR spectrum (400 MHz; CDCl₃) δ (ppm): 1.14 (s, 3H: —CH₃ 16 or 17); 1.25 (s, 3H: —CH₃ 16 or 17); 1.32 (s, 9H: —C(CH₃)₃); 1.76 (s, 3H: —CH₁₉); 1.86 (up, 1H: —(CH)—H 6); 1.93 (s, 3H: —CH₃ 18); 2.22 (dd, 1H, J=9 and 16 Hz: —(CH)—H 14); 2.37 (dd, 1H, J=9 and 16 Hz: —(CH)—H 14); 2.45 (s, 3H: —COCH₃); 2.6 (up, 1H: —(CH)—H 6); 3.35 (s, 1H: —OH 2'); 3.94 (d, 1H, J=7 Hz: —H 3); 4.26 (AB, 2H, J_{AB}=9 Hz: —CH₂—20); 4.28 (dd, 1H, J=7 and 12 Hz: —H 7); 4.62 (up, 1H: —H 2'); 4.98 (d, 1H, J=9 Hz: —H 5); 5.23 (s, 1H: —H 10); 5.45 and 5.58 (d and d, 1H each, J=10 Hz: —CH—NHCO—); 5.7 (d, 1H, J =7 Hz: —H 2); 6.28 (t, 1H, J=9 Hz: —H 13); 7.06 to 7.4 (up, 4H: F—C₆H₄); 7.5 [t, 2H, J=8 Hz: —OCOC₆H₅ (—H 3 and —H 5)]; 7.61 [t, 1H, J=8 Hz: —OCOC₆H₅ (—H 4)]; 8.13 [ d, 2H, J=8 Hz: —OCOC₆H₅ (—H 2 and H 6)].

Using the procedure described in Example 1, but employing suitable starting materials, the following intermediates are prepared:

4-acetoxy-2α-benzoyloxy-5β,20-epoxy-1-hydroxy-9-oxo-7β,10β-bis[(2,2,2-trichloroethoxy)carbonyloxy]-11-taxen-13α-yl (2R,3S)-3-tert-butoxycarbonylamino-3-(2-fluorophenyl)-2-hydroxypropionate, in the form of a white meringue-like product.

4-acetoxy-2α-benzoyloxy-5β,20-epoxy-1-hydroxy-9-oxo-7β,10β-bis[(2,2,2-trichloroethoxy)carbonyloxy]-11-taxen-13α-yl (2R,3S)-3-amino-2-hydroxy-3-(2-fluorophenyl)propionate, in the form of a white meringue-like product.

4-acetoxy-2α-benzoyloxy-5β,20-epoxy-1-hydroxy-9-oxo-7β,10β-bis[(2,2,2-trichloroethoxy)carbonyloxy]-11-taxen-13α-yl (4S,5R)-3-tert-butoxycarbonyl-2,2-dimethyl-4-(2-fluorophenyl)-5-oxazolidinecarbonate, in the form of a white meringue-like product.

(4S,5R)-3-tert-butoxycarbonyl-2,2-dimethyl-4-(2-fluorophenyl)-5-oxazolidinecarboxylic acid, in the form of white crystals, melting point 164° C.

ethyl (4S,5R)-3-tert-butoxycarbonyl-2,2-dimethyl-4-(2-fluorophenyl)-5-oxazolidinecarboxylate, in the form of a yellow oil.

ethyl (2R,3S)-3-tert-butoxycarbonylamino-2-hydroxy-3-(2-fluorophenyl)propionate, in the form of white crystals, melting point 99° C.

ethyl (2R,3S)-3-amino-2-hydroxy-3-(2-fluorophenyl)propionate, in the form of white crystals, melting point 73° C.

ethyl (2R,3S)-3-azido-2-hydroxy-3-(2-fluorophenyl)propionate, in the form of a yellow oil.

ethyl (2R,3R)-3-(2-fluorophenyl)-2-oxiranecarboxylate, in the form of a yellow oil.

(4S,5R)-3-[(2S,3R)-2-bromo-3-hydroxy-3-(2-fluorophenyl)-1-oxopropyl]-4-methyl-5-phenyl-2-oxazolidinone, in the form of a yellow meringue-like product

EXAMPLE 3

Using the procedure described in Example 1, but starting with 4-acetoxy-2α-benzoyloxy-5β,20-epoxy-1-hydroxy-9-oxo-7β,10β-bis[(2,2,2-trichloroethoxy)carbonyloxy]-11-taxen-13α-yl (2R,3S)-3-tert-butoxycarbonylamino-3-(4-chlorophenyl)-2-hydroxypropionate, 0.35 g of 4-acetoxy-2α-benzoyloxy-5β-20-epoxy-1,7β,10β-trihydroxy-9-oxo-11-taxen-13α-yl (2R,3S)-3-tert-butoxycarbonylamino-3-(4-chlorophenyl )-2-hydroxypropionate is obtained in the form of a white meringue-like product, the characteristics of which are as follows:

rotatory power: $[\alpha]_D^{20}=-27°$ (c=0.97; methanol)

NMR spectrum (400 MHz; CDCl$_3$) δ (ppm): 1.15 (s, 3H: —CH 16 or 17); 1.25 (s, 3H: —CH$_3$ 16 or 17); 1.35 (s, 9H: —C(CH$_3$)$_3$); 1.77 (s, 3H: —CH$_3$ 19); 1.9 (up, 1H: —(CH)—H 6 and s, 3H: —CH 18); 2.3 (d, 2H, J=8.5 Hz: —CH 14); 2.39 (s, 3H: —COCH$_3$); 2.6 (up, 1H: —(CH)—H 6 ); 3.48 (s, 1H: —OH 2'); 3.92 (d, 1H, J=7 Hz: —H 3); 4.24 (dd, 1H, J=7 and 12 Hz: —H 7); 4.26 (AB, 2H, J$_{AB}$=9 Hz: —CH$_2$—20); 4.61 (s, 1H: —H 2'); 4.96 (d, 1H, J=9 Hz: —H 5); 5.24 (s, 1H: —H 10); 5.26 (up, 1H: —H 3'); 5.43 (d, 1H, J=9 Hz: —NHCO—); 5.68 (d, 1H, J=7 Hz: —H 2); 6.25 (t, 1H, J=8.5 Hz: —H 13); 7.35 (up, 4H: Cl—C$_6$H$_4$); 7.5 [t, 2H, J=8 Hz: —OCOC$_6$H$_5$ (—H 3 and —H 5); 7.62 [ t, 1H, J=8 Hz: —OCOC$_6$H$_5$ (—H 4)]; 8.10 [d, 2H, J=8 Hz: —OCOC$_6$H$_5$ (—H and —H 6)].

Using the procedure described in Example 1, but employing suitable starting materials, the following intermediates are prepared:

4-acetoxy-2α-benzoyloxy-5β,20-epoxy-1-hydroxy-9-oxo-7β,10β-bis[(2,2,2-trichloroethoxy)carbonyloxy]-11-taxen-13α-yl (2R,3S)-3-tert-butoxycarbonylamino-3-(4-chlorophenyl)-2-hydroxypropionate, in the form of a white meringue-like product.

4-acetoxy-2α-benzoyloxy-5β,20-epoxy-1-hydroxy-9-oxo-7β,10β-bis[(2,2,2-trichloroethoxy)carbonyloxy]-11-taxen-13α-yl (2R,3S)-3-amino-2-hydroxy-3-(4-chlorophenyl)propionate, in the form of a white meringue-like product.

4-acetoxy-2α-benzoyloxy-5β,20-epoxy-1-hydroxy-9-oxo-7β,10β-bis[(2,2,2-trichloroethoxy)carbonyloxy]-11-taxen-13α-yl (4S,5R)-3-tert-butoxycarbonyl-2,2-dimethyl-4-(4-chlorophenyl)-5-oxazolidinecarboxylate, in the form of a white meringue-like product.

(4S, 5R)-3-tert-butoxycarbonyl-2,2-dimethyl-4-(4chlorophenyl)-5-oxazolidinecarboxylic acid, in the form of a colorless oil.

ethyl (4S,5R)-3-tert-butoxycarbonyl-2,2-dimethyl-4-(4-chlorophenyl)-5-oxazolidinecarboxylate, in the form of a yellow oil.

ethyl (2R,3S)-3-tert-butoxycarbonylamino-2-hydroxy-3-(4-chlorophenyl)propionate, in the form of cream-colored crystals, melting point 117° C.

ethyl (2R,3S)-3-amino-2-hydroxy-3-(4-chlorophenyl)propionate, in the form of a brown oil.

ethyl (2R,3S)-3-azido-2-hydroxy-3-(4-chlorophenyl)propionate, in the form of a yellow oil.

ethyl (2R,3R)-3-(4-chlorophenyl)-2-oxiranecarboxylate, in the form of a yellow oil.

(4S,5R)-3-[(2S,3R)-2-bromo-3-hydroxy-3-(4-chlorophenyl)-1-oxopropyl]-4-methyl-5-phenyl-2-oxazolidinone, in the form of white crystals, melting point 140C.

EXAMPLE 4

Using the procedure described in Example 1, but starting with 4-acetoxy-2α-benzoyloxy-5β,20-epoxy-1-hydroxy-9-oxo-7β,10β-bis[(2,2,2-trichloroethoxy)carbonyloxy]-11-taxen-13α-yl (2R,3S)-3-tert-butoxycarbonylamino-3-(4-methoxyphenyl)-2-hydroxypropionate, 0.15 g of 4-acetoxy-2α-benzoyloxy-5β,20-epoxy-1,7β,10β-trihydroxy-9-oxo-11-taxen-13α-yl (2R,3S)-3-tert-butoxycarbonylamino-3-(4-methoxyphenyl)-2-hydroxypropionate is obtained in the form of a white meringue-like product, the characteristics of which are as follows:

rotatory power: [α]$_D^{20}$=−32° (c=0.47; methanol)

NMR spectrum (400 MHz; CDCl$_3$) δ (ppm): 1.15 (s, 3H: —CH$_3$ 16 or 17); 1.25 (s, 3H: —CH$_3$ 16 or 17); 1.38 (s, 9H: —C(CH$_3$)$_3$); 1.7 (up, 1H: —OH 1); 1.78 (s, 3H: —CH$_3$ 19); 1.88 (up, 1H: —(CH)—H 6 and s, 3H: —CH$_3$ 18); 2.28 (d, 2H, J=8.5 Hz: —CH$_2$ 14); 2.38 (s, 3H: —COCH$_3$); 2.6 (up, 1H: —(CH)—H 6); 3.4 (up, —OH 2'); 3.8 (s, 3H: —C$_6$H$_4$—OCH$_3$); 3.92 (d, 1H, J=7 Hz: —H 3); 4.2 and 4.33 (2d, 1H each, J=9: Hz: —CH$_2$ 20); 4.25 (up, 1H: —H 7); 4.1 to 4.4 (broad up, 1H: —OH 10); 4.59 (up, 1H: —H 2'); 4.95 (d, 1H, J=9 Hz: —H 5); 5.2 and 5.37 (2 up, 1H each: —CH-N HCOO—); 5.22 (s, 1H: —H 10); 5.69 (d, 1H, J=7 Hz: —H 2); 6.22 (t, 1H, J=8.5 Hz: —H 13); 6.92 [d, 2H, J=8 Hz: —C$_6$H$_4$—OCH$_3$ (—H 3 and —H 5 ) ]; 7.31 [ d, 2H, J=8 Hz: —C$_6$H$_4$— OCH$_3$ (—H 2 and —H 6)]; 7.45 [t, 2H, J=8 Hz: —OCOC$_6$H$_5$ (—H 3 and —H 5)]; 7.62 [t, 1H, J=8 Hz: —OCOC$_6$H$_5$ (—H 4)]; 8.11 [d, 2H, J=8 Hz: —OCOC$_6$H$_5$ (—H 2 and —H 6 ) ].

Using the procedure described in Example 1, but employing suitable starting materials, the following intermediates are prepared:

4-acetoxy-2α-benzoyloxy-5β,20-epoxy-1-hydroxy-9-oxo-7β,10β-bis[(2,2,2-trichloroethoxy)carbonyloxy]-11-taxen-13α-yl (2R,3S)-3-tert-butoxycarbonylamino-3-(4-methoxyphenyl)-2-hydroxypropionate, in the form of a white meringue-like product.

4-acetoxy-2α-benzoyloxy-5β,20-epoxy-1-hydroxy-9-oxo-7β,10β-bis[(2,2,2-trichloroethoxy)carbonyloxy]-11-taxen-13α-yl (2R,3S)-3-amino-2-hydroxy-3-(4-methoxyphenyl)-2-hydroxypropionate, in the form of a white meringue-like product.

4-acetoxy-2α-benzoyloxy-5β,20-epoxy-1-hydroxy-9-oxo-7β,10β-bis[(2,2,2-trichloroethoxy)carbonyloxy]-11-taxen-13α-yl (4S,5R)-3-tert-butoxycarbonylamino-2,2-dimethyl-4-(4-methoxyphenyl)-5-oxazolidinecarboxylate, in the form of a white meringue-like product.

(4S,5R)-3-tert-butoxycarbonyl-2,2-dimethyl-4-(4-methoxyphenyl)-5-oxazolidinecarboxylic acid, in the form of a white meringue-like product.

ethyl (4S,5R)-3-tert-butoxycarbonyl-2,2-dimethyl-4-(4-methoxyphenyl)-5-oxazolidinecarboxylate, in the form of a yellow oil.

ethyl (2R,3S)-3-tert-butoxycarbonylamino-2-hydroxy-3-(4-methoxyphenyl)propionate, in the form of white crystals, melting point 135° C.

ethyl (2R,3S)-3-amino-2-hydroxy-3-(4methoxyphenyl)propionate, in the form of a yellow oil.

ethyl (2R,3S)-3-azido-2-hydroxy-3-(4-methoxyphenyl)propionate, in the form of a yellow oil.

ethyl (2R,3R)-3-(4-methoxyphenyl)-2-oxiranecarboxylate, in the form of a yellow oil.

(4S,5R)-3-[(2S,3R)-2-bromo-3-hydroxy-3-(4-methoxyphenyl)- 1-oxopropyl]-4-methyl-5phenyl-2oxazolidinone, in the form of white crystals, melting point 130° C.

EXAMPLE 5

Using the procedure described in Example 1, but starting with 4-acetoxy-2α-benzoyloxy-5β,20-epoxy-1-hydroxy-9-oxo-7β,10β-bis[(2,2,2-trichloroethoxy)carbonyloxy]-11-taxen-13α-yl (2R,3S)-3-tert-butoxycarbonylamino- 3-(4-fluorophenyl)-2-hydroxypropionate, 0.086 g of 4-acetoxy-2α-benzoyloxy-5β,20-epoxy-1,7β,10β-trihydroxy-9-oxo-11-taxen-13α-yl(2R,3S)-3-tert-butoxycarbonylamino-3-(4-fluorophenyl)-2-hydroxypropionate is obtained in the form of a white meringue-like product, the characteristics of which are as follows:

rotatory power: $[\alpha]_D^{20} = -35°$ (c=0.49; methanol)

NMR spectrum (250 MHz; CDCl$_3$) δ (ppm): 1.14 (s, 3H: —CH$_3$ 16 or 17); 1.25 (s, 3H: —CH$_3$ 16 or 17); 1.35 (s, 9H: —C(CH$_3$)$_3$); 1.7 (up, 1H: —OH 1); 1.77 (s, 3H: —CH$_3$ 19); 1.87 (up, 1H: —(CH)—H 6); 1.87 (s, 3H: —CH$_3$ 18); 2.3 (d, 2H, J=9 Hz: —C—H$_2$ 14); 2.36 (s, 3H: —COCH$_3$); 2.6 (up, 1H: —(CH)—H 6); 3.43 (up, 1H: —OH 2'); 3.93 (d, 1H, J=7 Hz: —H 3); 4.2 and 4.33 (AB, 2H, J$_{A-B}$=8 Hz: —CH$_2$ 20); 4.23 (up, 1H: —H 7); 4.6 (up, 1H: —H 2'); 4.96 (dd, 1H, J=2 and 10.5 Hz: —H5); 5.22 (s, 1H: H 10); 5.25 (up, 1H: —H 3'); 5.42 (d, 1H, J=10 Hz: —CH—NHCO—); 5.7 (dd, 1H, J=7 Hz: —H 2); 6.24 (t, 1H, J=9 Hz: —H 13); 7.09 [t, 2H, J=8.5 Hz: F-C$_6$H$_4$ (—H 3 and —H 5)]; 7.38 [dd, 2H, J=8.5 Hz: F-C$_6$H$_4$ (—H 2 and —H 6)]; 7.5 [t, 2H, J=8.5 Hz: —OCOC$_6$H$_5$ (—H 3 and —H 5)]; 7.62 [t, 1H, J=8.5 Hz: —OCOC$_6$H$_5$ (—H 4)]; 8.1 [d, 2H, J=8.5 Hz: —OCOC$_6$H$_5$ (—H 2 and —H 6)].

Using the procedure described in Example 1, but employing suitable starting materials, the following intermediates are prepared:

4-acetoxy-2α-benzoyloxy-5β,20-epoxy-1-hydroxy-9-oxo-7β,10β-bis[(2,2,2-trichloroethoxy)carbonyloxy]-11-taxen-13α-yl (2R,3S)-3-tert-butoxycarbonylamino-3-(4-fluorophenyl)-2-hydroxypropionate, in the form of a white meringue-like product.

4-acetoxy-2α-benzoyloxy-5β,20-epoxy-1-hydroxy-9-oxo-7β,10β-bis[(2,2,2-trichloroethoxy)carbonyloxy]-11-taxen-13α-yl (2R,3S)-3-amino-2-hydroxy-3-(4fluorophenyl)propionate, in the form of a white meringue-like product.

4-acetoxy-2α-benzoyloxy-5β,20-epoxy-1-hydroxy-9-oxo-7β,10β-bis[(2,2,2-trichloroethoxy)carbonyloxy]-11-taxen-13α-yl (4S,5R)-3-tert-butoxycarbonyl-2,2-dimethyl-4-(4-fluorophenyl)-5-oxazolidinecarboxylate, in the form of a white meringue-like product.

(4S,5R)-3-tert-butoxycarbonyl-2,2-dimethyl-4-(4-fluorophenyl)-5-oxazolidinecarboxylic acid, in the form of a yellow oil.

ethyl (4S,5R)-3-tert-butoxycarbonyl-2,2-dimethyl-4-(4-fluorophenyl)-5-oxazolidinecarboxylate, in the form of a yellow oil.

ethyl (2R,3S)-3-tert-butoxycarbonylamino-2-hydroxy-3-(4-fluorophenyl)propionate, in the form of white crystals, melting point 116° C.

ethyl (2R,3S)-3-amino-2-hydroxy-3-(4-fluorophenyl)propionate, in the form of white crystals, melting point 105° C.

ethyl (2R,3S)-3-azido-2-hydroxy-3-(4-fluorophenyl)propionate, in the form of a yellow oil.

ethyl (2R,3S)-3-(4-fluorophenyl)-2-oxiranecarboxylate, in the form of pale yellow crystals, melting point 40° C.

(4S,5R)-3-[(2S,3R)-2-bromo-3-hydroxy-3-(4-fluorophenyl)-1-oxopropyl]-4-methyl-5-phenyl-2-oxazolidinone, in the form of a yellow meringue-like product.

EXAMPLE 6

3.55 g of N,N'-dicyclohexylcarbodiimide are added to a solution of 5.52 g of (4S,5R)-3-tert-butoxycarbonyl-2,2-dimethyl-4-phenyl-5oxazolidinecarboxylic acid in 350 cm$^3$ of toluene. The solution is stirred for 10 minutes at a temperature in the region of 20° C. and 3 g of 4,10β-diacetoxy-2αbenzoyloxy-5β,20-epoxy-1,13α-dihydroxy-9-oxo-7β-triethylsilyloxy-11-taxene [prepared according to the method described by J-N. Denis et al., J. Am. Chem. Soc., 110, 5917 (1988)] and 0.52 g of 4-(dimethylamino)pyridine are then added. The reaction medium is then heated for 2 hours to a temperature in the region of 80° C. and, after the reaction mixture has been cooled to a temperature in the region of 20° C., 250 cm$^3$ of saturated aqueous sodium hydrogen carbonate solution are added. The aqueous phase is separated after settling has taken place and then extracted with 2 times 200 cm$^3$ of dichloromethane. The combined organic phases are dried over magnesium sulphate, filtered and then concentrated to dryness under reduced pressure (2.7 kPa) at a temperature in the region of 30° C. 10.8 g of an orange-colored oil are obtained, which product is purified by flash chromatography [eluent: dichloromethane/methanol (99.5:0.5 by volume)]. After concentration of fractions 60 to 73 to dryness under reduced pressure (2.7 kPa) at a temperature in the region of 40° C., 3.7 g of 4,10β-diacetoxy-2α-benzoyloxy-5β,20-epoxy-1-hydroxy-9-oxo-7β-triethylsilyloxy-11-taxen-13α-yl (4S,5R)-3-tert-butoxycarbonyl-2,2-dimethyl-4-phenyl-5-oxazolidinecarboxylate are obtained in the form of a yellow meringue-like product, the characteristics of which are as follows:

rotatory power: $[\alpha]_D^{20} = -45.3°$ (c=0.5; methanol)

| NMR spectrum (400 MHz; shifts in ppm) | |
| --- | --- |
| 7.35 ppm | up, 5H, C$_6$H$_5$ (chain) |
| 6.5 ppm | s, 1H, H-10 |
| 6.25 ppm | t, 1H, H-13 |
| 5.15 ppm | up, 1H, CHN (H-4') |
| 4.5 ppm | up, 2H, CHO (H-5') + H-7 |
| 4.15 and 4.25 ppm | 2d, 2H, H-20 |
| 1.25 ppm | s, 15H, C(CH$_3$)$_3$ + 2 CH$_3$ of the taxene ring |
| 0.98 ppm | t, 9H, CH$_3$CSi |
| 0.6 ppm | q, 6H, CH$_2$Si |

3 g of 4,10β-diacetoxy-2α-benzoyloxy-5β,20-epoxy-1-hydroxy-9-oxo-7β-triethylsilyloxy-11-taxen--13α-yl(4S,5R)-3-tert-butoxycarbonyl-2,2-dimethyl-4-phenyl-5-oxazolidinecarboxylate are added to 60 cm$^3$ of a 0.1N ethanolic solution, maintained at 0° C., of gaseous hydrochloric acid. The reaction medium is stirred for 48 hours at 0° C., and 250 cm$^3$ of dichloromethane is then added, followed by a mixture of 30 cm$^3$ of saturated aqueous sodium hydrogen carbonate solution and 30 cm$^3$ of water. The organic phase is separated after settling has taken place, dried over magnesium sulphate, filtered and then concentrated to dryness under reduced pressure (2.7 kPa) at a temperature in the region of 30° C. 2.8 g of a white meringue-like product are obtained, which product is purified by flash chromatography [eluent: dichloromethane/methanol (99:1 by volume)]. After concentration of fractions 15 to 30 to dryness under reduced pressure (2.7 kPa) at a temperature in the region of 40° C., 2.33 g of 4,10β-diacetoxy-2α-benzoyloxy-5β,20-epoxy-1,7β-dihydroxy-9-oxo-11-taxen-13α-yl (4S,5R)-3-tert-butoxycarbonyl-2,2-dimethyl-4-phenyl-5-oxazolidinecarboxylate are obtained in the form of a yellow meringue-like product, the characteristics of which are as follows:

rotatory power: $[\alpha]_D^{20} = -65.1°$ (c=1; methanol)

| NMR spectrum (250 MHz; shifts in ppm) | |
|---|---|
| 7.35 ppm | up, 5H, $C_6H_5$ (chain) |
| 6.3 ppm | up, 2H, H-10 and H-13 |
| 5.1 ppm | up, 1H, CHN (H-4') |
| 4.5 ppm | d, 1H, CHO (H-5') |
| 4.45 ppm | up, 1H, H-7 |
| 4.1 and 4.3 ppm | 2d, 2H, H-20 |
| 1.05 to 1.15 ppm | up, 9H, $C(CH_3)_3$ |

0.4 cm³ of 2,2,2-trichloroethyl chloroformate is added dropwise in the course of 10 minutes to a solution of 2.3 g of 4,10β-diacetoxy-2α-benzoyloxy-5β,20-epoxy-1,7β-dihydroxy-9-oxo-11-taxen-13α-yl (4S,5R)-3-tert-butoxycarbonyl-2,2-dimethyl-4-phenyl-5-oxazolidinecarboxylate in 35 cm³ of pyridine. The reaction medium is heated to 80° C. for 1 hour and 0.36 cm³ of 2,2,2-trichloroethyl chloroformate is then added. The reaction medium is maintained for 4 hours at 80° C., 0.36 cm³ of 2,2,2-trichloroethyl chloroformate is then added and the temperature is maintained at 80° C. for 30 minutes. After the reaction medium has been cooled to a temperature in the region of 20° C., 175 cm³ of water; 175 cm³ of saturated aqueous sodium hydrogen carbonate solution and 150 cm³ of dichloromethane are added. The aqueous phase is separated after settling has taken place and then extracted with 2 times 25 cm³ of dichloromethane. The combined organic phases are dried over magnesium sulphate, filtered and then concentrated to dryness under reduced pressure (0.13 kPa) at a temperature in the region of 30° C. 2.8 g of a white meringue-like product are obtained, which product is purified by flash chromatography [eluent: dichloromethane/methanol (99:1 by volume)]. After concentration of fractions 28 to 42 to dryness under reduced pressure (2.7 kPa) at a temperature in the region of 40° C. 2 57 g of 4,10β-diacetoxy-2α-benzoyloxy-5β,20-epoxy-1-hydroxy-9-oxo-7β-[(2,2,2-trichloroethoxy)carbonyloxy]-11-taxen-13α-yl (4S,5R)-3-tert-butoxycarbonyl-2,2-dimethyl-4-phenyl-5-oxazolidinecarboxylate are obtained in the form of a white meringue-like product, the characteristics of which are as follows:

rotatory power: $[\alpha]_D^{20} = -55°$ (c=0.5; methanol)

| NMR spectrum (400 MHz; shifts in ppm) | |
|---|---|
| 7.35 ppm | up, 5H, $C_6H_5$ (chain) |
| 6.4 ppm | s, 1H, H-10 |
| 6.25 ppm | t, 1H, H-13 |
| 5.6 ppm | dd, 1H, H-7) |
| 5.1 ppm | up, 1H, CHN (H-4') |
| 5.05 and 4.65 ppm | 2d, 2H, $CH_2CCl_3$ |
| 4.5 ppm | d, 1H, CHO (H-5') |
| 4.1 and 4.3 ppm | 2d, 2H, H-20 |
| 1.05 to 1.15 ppm | up, 9H, $C(CH_3)_3$ |

A solution of 3.2 g of 4,10β-diacetoxy-2α-benzoyloxy-5β,20-epoxy-1-hydroxy-9-oxo-7β-[(2,2,2-trichloroethoxy)carbonyloxy]-11-taxen-13α-yl (4S,5R)-3-tert-butoxycarbonyl-2,2-dimethyl-4-phenyl-5-oxazolidinecarboxylate in 32 cm³ of formic acid is stirred for 4.5 hours at a temperature in the region of 20° C. The reaction medium is concentrated to dryness under reduced pressure (0.13 kPa) at a temperature in the region of 30° C. The residue obtained is dissolved in 150 cm³ dichloromethane and this solution is washed with 50 cm³ of saturated aqueous sodium hydrogen carbonate solution, dried over magnesium sulphate, filtered and concentrated to dryness under reduced pressure (0.13 kPa) at a temperature in the region of 30° C. 2.74 g of a cream-colored meringue-like product are obtained, which product is purified by flash chromatography [eluent: dichloromethane/methanol (99:1 by volume)]. After concentration of fractions 13 to 25 to dryness under reduced pressure (2.7 kPa) at a temperature in the region of 40° C. 2 17 g of 4,10β-diacetoxy-2α-benzoyloxy-5β,20-epoxy-1-hydroxy-9-oxo-7β-[(2,2,2-trichloroethoxy)carbonyloxy]-11-taxen-13α-yl (2R,3S)-3-amino-2-hydroxy-3-phenylpropionate are obtained in the form of a white meringue-like product, the characteristics of which are as follows:

rotatory power: $[\alpha]_D^{20} = -60.2°$ (c=0.5; methanol)

| NMR spectrum (400 MHz; shifts in ppm) | |
|---|---|
| 7.4 to 7.25 ppm | up, 5H, $C_6H_5$ (chain) |
| 6.4 ppm | s, 1H, H-10 |
| 6.15 ppm | t, 1H, H-13 |
| 5.55 ppm | dd, 1H, H-7 |
| 5.05 and 4.65 ppm | 2d, 2H, $CH_2CCl_3$ |
| 4.35 ppm | up, 2H, H-2' and H-3' |
| 4.15 and 4.3 ppm | 2d, 2H, H-20 |

4,10β-Diacetoxy-2α-benzoyloxy-5β,20-epoxy-1-hydroxy-9-oxo-7β-[(2,2,2-trichloroethoxy)carbonyloxy]-11-taxen-13α-yl (2R,3S)-3-amino-2-hydroxy-3-phenylpropionate may also be prepared in the following manner:

A solution of 0.1 g of 4,10β-diacetoxy-2α-benzoyloxy-5β,20-epoxy-1-hydroxy-9-oxo-7β-[(2,2,2trichloroethoxy)carbonyloxy]-11-taxen-13α-yl (4S,5R)-3-tert-butoxycarbonyl-2,2-dimethyl-4-phenyl-5-oxazolidinecarboxylate in a mixture of 1.4 cm³ of a 3.4N ethanolic solution of gaseous hydrochloric acid and 0.6cm³ of dichloromethane is stirred for 7 hours at a temperature in the region of 20° C. 2 cm³ of dichloromethane, 1 cm³ of water and 1 cm³ of saturated aqueous sodium hydrogen carbonate solution are then added to the reaction medium. The organic phase is separated after settling has taken place, dried over magnesium sulphate, filtered and concentrated to dryness under reduced pressure (0.13 kPa) at a temperature in the region of 30° C. 0.1 g of a yellow meringue-like product is obtained, which product is purified by flash chromatography [eluent: dichloromethane/methanol (98:2 by volume)]. After concentration of fractions 14 to 20 to dryness under reduced pressure (2.7 kPa) at a temperature in the region of 40° C., 0.023 g of 4,10β-diacetoxy-2α-benzoyloxy-5β,20-epoxy-1-hydroxy-9-oxo-7β-[(2,2,2-trichloroethoxy)carbonyloxy]-11-taxen-13α-Yl (2R,3S)-3-amino-2-hydroxy-3-phenylpropionate is obtained in the form of a white meringue-like product.

A mixture of 140 cm³ of saturated aqueous sodium hydrogen carbonate solution and 140 cm³ of water is added to a stirred solution of 2.1 g of 4,10β-diacetoxy-2α-benzoyloxy-5β,20-epoxy-1-hydroxy-9-oxo-7β-[(2,2,2-trichloroethoxy)carbonyloxy]-11-taxen-13α-yl (2R,3S)-3-amino-2-hydroxy-3-phenylpropionate in 52.5 cm³ of ethyl acetate. 0,277 cm³ of benzoyl chloride is then added in the course of 2 minutes. The reaction medium is stirred for 15 minutes at a temperature in the region of 24° C. and the aqueous phase is separated after settling has taken place and then extracted with 3 times 50 cm³ of dichloromethane. The combined organic phases are dried over magnesium sulphate, filtered and then concentrated to dryness under reduced pressure (2.7 kPa) at a temperature in the region of 30° C. 2.3 g of a cream-colored meringue-like product are obtained, which product is purified by flash chromatography [eluent: dichloromethane/methanol (99:1 by volume)]. After concentration of fractions 31 to 38 to dryness under reduced pressure (2.7 kPa) at a temperature in the region of 40° C., 2.03 g of 4,10β-diacetoxy-2α-benzoyloxy-5β,20-epoxy-1-hydroxy-9-oxo-7β-[(2,2,2-trichloroethoxy)carbonyloxy]-11-taxen-13-yl (2R,3S)-3-benzoylamino-2-hydroxy-3-phenylpropionate are obtained in the form of a white meringue-like product, the characteristics of which are as follows:

rotatory power: $[\alpha]_D^{20} = -41.9°$ (c=0.5; methanol)

| NMR spectrum (250 MHz; shifts in ppm) | |
|---|---|
| 8.15 ppm | d, 2H ] |
| 7.8 ppm | d, 2H ] 2 × C$_6$H$_5$CO + C$_6$H$_5$ (chain) |
| 7.6 ppm | t, 1H ] |
| 7.6 to 7.3 ppm | up, 10 H] |
| 7.05 ppm | d, 1H, NH |
| 6.35 ppm | s, 1H, H-10 |
| 6.2 ppm | t, 1H, H-13 |
| 5.8 ppm | dd, 1H, H-3' |
| 5.55 ppm | dd, 1H, H-7 |
| 5.05 and 4.62 ppm | 2d, 2H, CH$_2$CCl$_3$ |
| 4.8 ppm | d, 1H, H-2' |
| 4.2 and 4.35 ppm | 2d, 2H, H-20 |

4,10β-Diacetoxy-2α-benzoyloxy-5β,20-epoxy-1-hydroxy-9-oxo-7β-[(2,2,2-trichloroethoxy)carbonyl]-11-taxen-13α-yl (2R,3S)-3-benzoylamino-2-hydroxy-3-phenylpropionate may be converted to taxol by replacement of the 2,2,2-trichloroethoxycarbonyl group by a hydrogen atom by means of zinc in the presence of acetic acid, according to the method described in European Patent EP 0,253,738.

(4S,5R)-3-tert-Butoxycarbonyl-2,2-dimethyl-4-phenyl-5-oxazolidinecarboxylic acid may be prepared in the following manner:

A solution of 4.62 g of lithium hydroxide hydrate in 80 cm³ of water is added in the course of 10 minutes to a stirred solution of 12.8 g of ethyl (4S,5R)-3-tert-butoxycarbonyl-2,2-dimethyl-4-phenyl-5-oxazolidinecarboxylate in 200 cm³ of ethanol. After stirring for a further 10 minutes, the reaction medium is concentrated to dryness under reduced pressure (2.7kPa) at a temperature in the region of 40° C. The residue obtained is dissolved in 70 cm³ of water and then extracted with 3 times 20 cm³ of isopropyl ether. The aqueous phase is then acidified to a pH in the region of 2.6 by adding approximately 100 cc of 1N aqueous hydrochloric acid solution and thereafter extracting with 3 times 50 cm³ of dichloromethane. The combined organic phases are dried over magnesium sulphate, filtered and then concentrated to dryness under reduced pressure (2.7 kPa) at a temperature in the region of 40° C. 11.3 g of (4S,5R)-3-tert-butoxycarbonyl-2,2-dimethyl-4-phenyl-5-oxazolidinecarboxylic acid are thereby obtained in the form of a yellow oil, the characteristics of which are as follows:

rotatory power: $[\alpha]_D^{20} = -3.3°$ (c=0.8; CHCl$_3$)

| NMR spectrum (250 MHz; shifts in ppm) | |
|---|---|
| 7.4 ppm | up, 5H, C$_6$H$_5$ |
| 5.2 ppm | up, 1H, CHN |

| -continued | |
|---|---|
| NMR spectrum (250 MHz; shifts in ppm) | |
| 4.55 ppm | d, 1H, CHO |
| 1.85 ppm | s, 3H, C—CH$_3$ |
| 1.75 ppm | s, 3H, C—CH$_3$ |
| 1.2 ppm | up, 9H, C(CH$_3$)$_3$ |

Ethyl (4S, 5R) -3-tert-butoxycarbonyl-2,2-dimethyl-4-phenyl-5-oxazolidinecarboxylate may be prepared in the following manner:

A solution of 11.7 g of ethyl (2R,3S)-3-tert-butoxycarbonylamino-2-hydroxy-3-phenylpropionate, 3.6 cm³ of 2-methoxypropene and 0.06 g of p-toluenesulphonic acid in 120 cm³ of toluene is stirred for 1 hour at a temperature in the region of 20° C. The reaction medium is brought to boiling and 0.06 g of p-toluenesulphonic acid is then added. The distillate is collected in a graduated vessel while a solution of 18 cm³ of 2-methoxypropene in 82 cm³ of toluene is added dropwise so as to keep the volume of the reaction medium constant. After distillation for 1 hour 20 minutes, 0.06 g of para-toluenesulphonic acid is added and distillation is continued for 10 minutes; the volume of distillate collected is then 100 cm³. The reaction medium is cooled to a temperature in the region of 20° C. and 25 cm³ of saturated aqueous sodium hydrogen carbonate solution are then added. The aqueous phase is separated after settling has taken place and then extracted with 2 times 10 cm³ of di-chloromethane; the combined organic phases are dried over magnesium sulphate, filtered and concentrated to dryness under reduced pressure (2.7 kPa) at a temperature in the region of 40° C. 20.8 g of a yellow oil are thereby obtained, which product is purified by chromatography on 630 g of silica gel [column diameter: 5.5 cm; eluent: cyclohexane/ethyl acetate (70:30 by volume), 100-cm³ fractions]. After concentration of fractions 3 to 9 to dryness under reduced pressure (2.7 kPa) at a temperature in the region of 40° C., 13 g of ethyl (4S,5R)-3-tert-butoxycarbonyl-2,2-dimethyl-4-phenyl-5-oxazolidinecarboxylate are obtained in the form of a yellow oil, the characteristics of which are as follows:

rotatory power: $[\alpha]_D^{20} = -7.3°$ (c=1; CHCl$_3$)

| NMR spectrum (250 MHz; shifts in ppm): | |
|---|---|
| 7.3 ppm | up, 5H, C$_6$H$_5$ |
| 5.05 ppm | up, 1H, CHN |
| 4.45 ppm | d, 1H, CHO |
| 4.25 ppm | q, 2H, OCH$_2$— |
| 1.8 ppm | s, 3H, C—CH$_3$ |
| 1.7 ppm | s, 3H, C—CH$_3$ |
| 1.3 ppm | t, 3H, O—C—CH$_3$ |
| 1.1 ppm | up, 9H, C(CH$_3$)$_3$ |

Ethyl (2R,3S)-3-tert-butoxycarbonylamino-2-hydroxy-3-phenylpropionate may be prepared according to the following method:

7.1 g of sodium hydrogen carbonate are added to a stirred solution of 16 g of ethyl (2R,3S)-3-amino-2-hydroxy-3-phenylpropionate in 160 cm³ of dichloromethane, and a solution of 22.1 g of di-tert-butyl dicarbonate in 40 cm³ of dichloromethane is then introduced in the course of 40 minutes. The reaction medium is stirred for 3.25 hours at a temperature in the region of 20° C. and 150 cm³ of water are then added. The organic phase is separated off after settling has taken place, the aqueous phase is extracted with 50 cm³ of dichloromethane and the combined organic phases are then dried over magnesium sulphate, filtered and concentrated to dryness under reduced pressure (2.7 kPa) at a temperature in the region of 30° C. The residue obtained is ground in 50 cm³ of isopropyl ether; the solid obtained is filtered off and then dried under reduced pressure (2.7 kPa) at a temperature in the region of 20° C. 11.9 g of ethyl (2R,3S)-3 -tert-butoxycarbonylamino-2-hydroxy-3-phenylpropionate are thereby obtained in the form of a white powder, melting point 124° C., the rotatory power of which is $[\alpha]_D^{20}$=6.3° (c=1; CHCl₃).

Ethyl (2R,3S)-3-amino-2-hydroxy-3-phenylpropionate may be prepared by the method described by H. Hönig et al., Tetrahedron, 46, p. 3841 (1990).

EXAMPLE 7

Using a procedure similar to that described in Example 6, but starting with 10 g of (4S,5R)-3 -tert-butoxycarbonyl-2,2-dimethyl-4-phenyl-5-oxazolidinecarboxylic acid and 12.6 g of 4-acetoxy-2α -benzoyloxy-5β,20-epoxy-1,13α-dihydroxy-9-oxo-7β,10β-bis[(2,2,2-trichloroethoxy)carbonyloxy]-11-taxene, and after purification by flash chromatography [eluent: dichloromethane/methanol (98:2 by volume)] and concentration of fractions 22 to 39 to dryness under reduced pressure (2.7 kPa) at a temperature in the region of 40° C., 14 g of 4-acetoxy-2α-benzoyloxy-5β,20 -epoxy-1-hydroxy-9-oxo-7β,10β-bis[(2,2,2-trichloroethoxy)carbonyloxy]-11-taxen-13α-yl (4S,5R)-3 -tert-butoxycarbonyl-2,2-dimethyl-4-phenyl-5-oxazolidinecarboxylate are obtained in the form of a white meringue-like product, the characteristics of which are as follows:

rotatory power: $[\alpha]_D^{20}$=−37.2° (c=1; methanol)

| NMR spectrum (400 MHz; shifts in ppm): | |
|---|---|
| 7.4 to 7.2 ppm | up, 5H, C₆H₅ (chain) |
| 6.25 ppm | t, 1H, H-13 |
| 6.2 ppm | s, 1H, H-10 |
| 5.55 ppm | dd, 1H, H-7 |
| 5.1 ppm | up, 1H, CHN (H-4') |
| 4.9 and 4.6 ppm | 2d, 2H, CH₂CCl₃ |
| 7.78 ppm | s, 2H, CH₂CCl₃ |
| 4.45 ppm | d, 1H, CHO (H-5') |
| 4.1 and 4.28 ppm | 2d, 2H, H-20 |
| 1.1 ppm | up, 9H, C(CH₃)₃ |

4-Acetoxy-2α-benzoyloxy-5,20-epoxy-1,13α -dihydroxy-9-oxo-7β,10β-bis[(2,2,2-trichloroethoxy)carbonyloxy]-11-taxene [sic] may be prepared according to the method described in European Patent EP 0,253,738.

EXAMPLE 8

Using a procedure similar to that described in Example 6, but starting with 14 g of 4-acetoxy-2α -benzoyloxy-5β,20-epoxy-1-hydroxy-9-oxo-7β,10β-bis[(2,2,2-trichloroethoxy)carbonyloxy]-11-taxen-13α-yl (4S,5R)-3-tert-butoxycarbonyl-2,2-dimethyl-4-phenyl-5-oxazolidinecarboxylate and after purification by flash chromatography [eluent: dichloromethane/methanol (95:5 by volume)] and concentration of fractions 7 and 8 to dryness under reduced pressure (2.7 kPa) at a temperature in the region of 40° C., 6.3 g of 4-acetoxy-2α-benzoyloxy-5β, 20-epoxy-1-hydroxy-9-oxo-7β,10β-bis[(2,2,2-trichloroethoxy)carbonyloxy]-11-taxen-13α-yl (2R,3S)-3-amino-2-hydroxy-3-phenylpropionate are obtained in the form of a white meringue-like product, the characteristics of which are as follows:

rotatory power: $[\alpha]_D^{20}$=−39.7° (c=1; methanol)

| NMR spectrum (400 MHz; shifts in ppm): | |
|---|---|
| 7.45 to 7.3 ppm | up, 5H, C₆H₅ (chain) |
| 6.3 ppm | s, 1H, H-10 |
| 6.22 ppm | t, 1H, H-13 |
| 5.6 ppm | dd, 1H, H-7 |
| 4.95 and 4.65 ppm | 2d, 2H, CH₂CCl₃ |
| 4.8 ppm | s, 2H, CH₂CCl₃ |
| 4.40 ppm | up, 3H, H-2' + H-3' + H-20 |
| 4.2 ppm | d, 1H, H-20 |

4-Acetoxy-2α-benzoyloxy-5β,20-epoxy-1 -hydroxy-9-oxo-7β,10β-bis[(2,2,2-trichloroethoxy)carbonyloxy]-11-taxen-13α-yl (2R,3S)-3 -amino-2-hydroxy-3-phenylpropionate is converted to 4 -acetoxy-2α-benzoyloxy-5β,20-epoxy-1-hydroxy-9-oxo-7β,10β-bis[(2,2,2-trichloroethoxy)carbonyloxy]-11 -taxen-13α-yl (2R,3S)-3-tert-butoxycarbonylamino-2 -hydroxy-3-phenylpropionate by the action of di-tert-butyl dicarbonate in the presence of an inorganic or organic base.

4-Acetoxy-2α-benzoyloxy-5β,20-epoxy-1 -hydroxy-9-oxo-7β,10β-bis[(2,2,2-trichloroethoxy)carbonyloxy]-11-taxen-13α-yl (2R,3S)-3 -tert-butoxycarbonylamino-2-hydroxy-3-phenylpropionate is converted to 4-acetoxy-2α-benzoyloxy-5β,20-epoxy-1,7β,10β -trihydroxy-9-oxo-11-taxen-13α-yl (2R,3S)-3 -tert-butoxycarbonylamino-2-hydroxy-3-phenylpropionate by replacement of the 2,2,2-trichloroethoxycarbonyl groups by a hydrogen atom by means of zinc in the presence of acetic acid, according to the method described in European Patent Application EP 0,253, 738.

EXAMPLE 9

Using a procedure similar to that described in Example 6, but starting with 0.54 g of (4SR,5RS)-3-tert-butoxycarbonyl-2,2-dimethyl-4-phenyl-5-oxazolidinecarboxylic acid and 0.47 g of 4-acetoxy-2α-benzoyloxy-5β, 10-epoxy-1,13α-dihydroxy-9-oxo-7β,10β-bis[(2,2,2-trichloroethoxy)carbonyloxy]-11-taxene, and after purification by flash chromatography [eluent: dichloromethane/methanol (99.5:0.5 by volume)] and concentration of fractions 9 to 11 to dryness under reduced pressure (2.7 kPa) at a temperature in the region of 40° C., 0.5 g of 4-acetoxy-2α-benzoyloxy-5β,20-epoxy-1-hydroxy-9-oxo-7β,10β-bis[(2,2,2-trichloroethoxy)carbonyloxy]-11-taxen-13β-yl (4S,5R)-3-tert-butoxycarbonyl-2,2-dimethyl-4-phenyl-5-oxazolidinecarboxylate is obtained in the form of a white meringue-like product, the characteristics of which are identical to those of the product obtained in Example 7.

(4SR,5RS)-3-tert-Butoxycarbonyl-2,2-dimethyl-4-phenyl-5-oxazolidinecarboxylic acid may be obtained under the conditions described in Example 6 for the preparation of (4S,5R)-3-tert-butoxycarbonyl-2,2-dimethyl-4-phenyl-5-oxazolidinecarboxylic acid.

Thus, starting with 5 g of ethyl (4SR,5RS)-3-tert-butoxycarbonyl-2,2-dimethyl-4-phenyl-5-oxazolidinecarboxylate, 4.54 g of (4SR,5RS)-3-tert-butoxycarbonyl-2,2-dimethyl-4-phenyl-5-oxazolidinecarboxylic acid are obtained in the form of a white solid, melting point 110° C., the characteristics of which are as follows:

| NMR spectrum (250 MHz; shifts in ppm): | |
|---|---|
| 7.4 ppm | up, 5H, $C_6H_5$ |
| 5.2 ppm | up, 1H, CHN |
| 4.55 ppm | d, 1H, CHO |
| 1.85 ppm | s, 3H, C—$CH_3$ |
| 1.75 ppm | s, 3H, C—$CH_3$ |
| 1.2 ppm | up, 9H, $C(CH_3)_3$ |

Ethyl (4SR,5RS)-3-tert-butoxycarbonyl-2,2-dimethyl-4-phenyl-5-oxazolidinecarboxylate may be prepared in the following manner:

A solution of 0.42 g of ethyl (2RS,3SR)-3-tert-butoxycarbonylamino-2-hydroxy-3-phenylpropionate, 4 cm³ of 2,2-dimethoxypropane and 0.01 g of p-toluene-sulphonic acid in 10 cm³ of toluene is brought to boiling for 15 minutes; 5 cm³ of distillate are collected. 5 cm³ of toluene and 1 cm³ of 2,2dimethoxypropane are then added and a further 5 cm³ of distillate are then distilled in the course of 15 minutes. This process is repeated twice. The reaction medium is cooled to a temperature in the region of 20° C. and 20 cm³ of saturated sodium hydrogen carbonate solution are then added. The aqueous phase is separated after settling has taken place and then extracted with 20 cm³ of dichloromethane; the combined organic phases are dried over magnesium sulphate, filtered and concentrated to dryness under reduced pressure (2.7 kPa) at a temperature in the region of 40° C. 0.42 g of a yellow oil is thereby obtained, which product is purified by chromatography on 15 g of silica gel (column diameter: 1.5 cm; eluent: dichloromethane; 10-cm³ fractions). After concentration of fractions 6 to 13 to dryness under reduced pressure (2.7 kPa) at a temperature in the region of 40° C. 0 2 g of ethyl (4SR,5RS)-3-tert-butoxycarbonyl-2,2-dimethyl-4-phenyl-5-oxazolidinecarboxylate is obtained in the form of a yellow oil, the characteristics of which are as follows:

| NMR spectrum (250 MHz; shifts in ppm): | |
|---|---|
| 7.3 ppm | up, 5H, $C_6H_5$ |
| 5.05 ppm | up, 1H, CHN |
| 4.45 ppm | d, 1H, CHO |
| 4.25 ppm | q, 2H, $OCH_2$— |
| 1.8 ppm | s, 3H, C—$CH_3$ |
| 1.7 ppm | s, 3H, C—$CH_3$ |
| 1.3 ppm | t, 3H, O—C—$CH_3$ |
| 1.1 ppm | up, 9H, $C(CH_3)_3$ |

Ethyl (2RS,3SR)-3-tert-butoxycarbonylamino-2-hydroxy-3-phenylpropionate may be prepared according to the method described in Example 6 for the preparation of ethyl (2R,3S)-3-tert-butoxycarbonylamino-2-hydroxy-3-phenylpropionate.

Thus, starting with 0.78 g of ethyl (2RS,3SR)-3-amino-2-hydroxy-3-phenylpropionate, 0.6 g of ethyl (2RS,3SR)-3-tert-butoxycarbonylamino-2-hydroxy-3-phenylpropionate is obtained in the form of a white powder, melting point 102° C.

Ethyl (2RS,3SR)-3-amino-2-hydroxy-3-phenylpropionate may be prepared by the method described by H.Hönig et al., Tetrahedron, 46, p. 3841 (1990).

EXAMPLE 10

Using a procedure similar to that described in Example 6, but starting with 1.7 g of (4S,5R)-3-tert-butoxy-carbonyl-2,2-diethyl-4-phenyl-5-oxazolidinecarboxylic acid and 2.9 g of 4-acetoxy-2α-benzoyloxy-5β,20-epoxy-1,13α-dihydroxy-9-oxo-7β,10β-bis[(2,2,2-trichloro-ethoxy)carbonyloxy]-11-taxene, 3.5 g of 4-acetoxy-2α-benzoyloxy-5β,20-epoxy-1-hydroxy-9-oxo-7β,10β-bis[(2,2,2-trichloroethoxy)carbonyloxy]-11-taxen-13α-yl (4S,5R)-3-tert-butoxycarbonyl-2,2-diethyl-4-phenyl-5-oxazolidinecarboxylate are obtained in the form of a white meringue-like product.

rotatory power: $[\alpha]_D^{20}=-41.2°$ (c=1; methanol).

4-Acetoxy-2β-benzoyloxy-5β,20-epoxy-1-hydroxy-9-oxo-7β,10β-bis[(2,2,2-trichloroethoxy)carbonyloxy]-11-taxen-13α-yl (4S,5R)-3-tert-butoxycarbonyl-2,2-diethyl-4-phenyl-5-oxazolidinecarboxylate is converted to 4-acetoxy-2α-benzoyloxy-5β,20-epoxy-1-hydroxy-9-oxo-7β,10β-bis[(2,2,2-trichloroethoxy)carbonyloxy]-11-taxen-13α-yl (2R,3S)-3-amino-2-hydroxy-3-phenylpropionate by the action of formic acid as described in Example 6 for 4-acetoxy-2α-benzoyloxy-5β,20-epoxy-1-hydroxy-9-oxo-7β,10β-bis[(2,2,2-trichloroethoxy)carbonyloxy]-11-taxen-13α-yl (4S,5R)-3-tert-butoxycarbonyl-2,2-dimethyl-4-phenyl-5-oxazolidinecarboxylate. The product thereby obtained possesses physical characteristics in all respects identical to those described in Example 9 [sic] for the same product.

rotatory power: $[\alpha]_D^{20}=-38.3°$ (c =0.8; methanol)

(4S,5R)-3-tert-Butoxycarbonyl-2,2-diethyl-4-phenyl-5-oxazolidinecarboxylic acid may be obtained under the conditions described in Example 6 for the preparation of (4S,5R)-3-tert-butoxycarbonyl-2,2-dimethyl-4-phenyl-5-oxazolidinecarboxylic acid. Thus, starting with 2.3 g of ethyl (4S,5R)-3-tert-butoxycarbonyl-2,2-diethyl-4-phenyl-5-oxazolidinecarboxylate, 1.7 g of (4S,5R)-3-tert-butoxycarbonyl-2,2-diethyl-4-phenyl-5-oxazolidinecarboxylic acid is obtained in the form of white crystals, melting point 185° C.

rotatory power: $[\alpha]_D^{20}=+2.4°$ (c=0.5; methanol).

Ethyl (4S,5R)-3-tert-butoxycarbonyl-2,2-dimethyl-4-phenyl-5-oxazolidinecarboxylate may be prepared in the following manner:

A solution of 2.5 g of ethyl (2R,3S)-3-tert-butoxycarbonylamino-2-hydroxy-3-phenylpropionate, 1.12 g of 3,3-dimethoxypentane and 25 mg of pyridinium p-toluene-sulphonate in 25 cm³ of toluene is stirred for 3 hours at a temperature in the region of 20° C. The reaction mixture is heated to boiling and the distillate is collected in a graduated vessel. After 20 cm³ of distillate have been collected, a solution of 1.12 g of 3,3-dimethoxypentane and 25 mg of pyridinium p-toluenesulphonate in 10 cm³ of toluene is added to the reaction medium and the mixture is heated to reflux of the toluene for 5 hours. The reaction medium is cooled to a temperature in the region of 20° C. and 10 cm³ of saturated aqueous sodium hydrogen carbonate solution are then added. The aqueous phase is separated after settling has taken place and then extracted with 2 times 10 cm³ of dichloromethane. The organic phases are combined, dried over magnesium sulphate, filtered and concentrated to dryness under reduced pressure (2.7 kPa) at a temperature in the region of 40° C. 2.3 g of ethyl (4S,5R)-3-tert-butoxycarbonyl-2,2-diethyl-4-phenyl-5-oxazolidinecarboxylate are thereby obtained in the form of a yellow oil.

rotatory power: $[\alpha]_D^{20}=-8.9°$ (c =1; methanol)

3,3-Dimethoxypentane may be prepared by the method described by Lorette et al., J. Org. Chem. 24, 1731, (1959).

EXAMPLE 11

Using a procedure similar to that described in Example 6, but starting with 0.9 g of (4S,5R)-3-tert-butoxycarbonyl-2-cyclohexanespiro-4-phenyloxazolidine-5-carboxylic [sic] acid and 1.443 g of 4-acetoxy-2α-benzoyloxy-5β,20-epoxy-1,13α-dihydroxy-9-oxo-7β,10β-bis[(2,2,2-trichloroethoxy)carbonyloxy]-11-taxene, 1.85 g of 4-acetoxy-2α-benzoyloxy-5β,20-epoxy-1-hydroxy-9-oxo-7β,10β-bis[(2,2,2-trichloroethoxy)carbonyloxy]-11-taxen-13α-yl (4S,5R)-3-tert-butoxycarbonyl-2-cyclohexanespiro-4-phenyloxazolidine-5-carboxylate [sic] is obtained in the form of a white meringue-like product.

4-Acetoxy-2α-benzoyloxy-5β,20-epoxy-1-hydroxy-9-oxo-7β,10β-bis[(2,2,2-trichloroethoxy)carbonyloxy]-11-taxen-13α-yl (4S,5R)-3-tert-butoxycarbonyl-2-cyclohexanespiro-4-phenyloxazolidine-5-carboxylate [sic] is converted to 4-acetoxy-2α-benzoyloxy-5β,20-epoxy-1-hydroxy-9-oxo-7β,10β-bis-[(2,2,2-trichloroethoxy)carbonyloxy]-11-taxen-13α-yl (2R,3S)-3-amino-2-hydroxy-3-phenylpropionate by the action of formic acid as described in Example 6 for 4-acetoxy-2α-benzoyloxy-5β,20-epoxy-1-hydroxy-9-oxo-7β,10β-bis[(2,2,2-trichloroethoxy)carbonyloxy]-11-taxen-13α-yl (4S,5R)-3-tert-butoxycarbonyl-2,2-dimethyl-4-phenyl-5-oxazolidinecarboxylate. The product thereby obtained possesses physical characteristics in all respects identical to those described in Example 8 for the same product.

rotatory power: $[\alpha]_D^{20}=-41.7°$ (c=0.5; methanol)

(4S,5R)-3-tert-Butoxycarbonyl-2-cyclohexanespiro-4-phenyl5-oxazolidinecarboxylic acid may be obtained under the conditions described in Example 6 for the preparation of (4S,5R)-3-tert-butoxycarbonyl-2,2-dimethyl-4-phenyl-5-oxazolidinecarboxylic acid. Thus, starting with 1.2 g of ethyl (4S,5R)-3-tert-butoxycarbonyl-2-cyclohexanespiro-4-phenyloxazolidine-5-carboxylate [sic], 1 g of (4S,5R)-3-tert-butoxycarbonyl-2-cyclohexanespiro-4-phenyl-5-oxazolidinecarboxylic acid is obtained in the form of a white meringue-like product.

rotatory power: $[\alpha]_D^{20}32 -4.5°$ (c=0.5; methanol)

Ethyl (4S,5R)-3-tert-butoxycarbonyl-2-cyclohexanespiro-4-phenyl-5-oxazolidinecarboxylate may be prepared in the following manner:

A solution of 2.5 g of ethyl (2R,3S)-3-tert-butoxycarbonylamino-2-hydroxy-3-phenylpropionate, 1.22 g of 1,1-dimethoxycyclohexane and 25 mg of pyridinium p-toluenesulphonate in 25 cm$^3$ of toluene is stirred for 3 hours at a temperature in the region of 20° C. The reaction mixture is heated to boiling and the distillate is collected in a graduated vessel. After 20 cm$^3$ of distillate have been collected, a solution of 1.22 g of 1,1-dimethoxycyclohexane and 25 mg of pyridinium p-toluenesulphonate in 10 cm$^3$ of toluene is added to the reaction medium and the mixture is heated to reflux of the toluene for 30 hours. The reaction medium is cooled to a temperature in the region of 20° C. and 10 cm$^3$ of saturated aqueous sodium hydrogen carbonate solution are then added. The aqueous phase is separated after settling has taken place and then extracted with 2 times 10 cm$^3$ of dichloromethane. The organic phases are combined, dried over magnesium sulphate, filtered and concentrated to dryness under reduced pressure (2.7 kPa) at a temperature in the region of 40° C. 2.6 g of a white meringue-like product are obtained, which product is purified by chromatography on 100 g of silica (0.063–0.2 mm) contained in a column 2 cm in diameter (eluent: dichloromethane), collecting 25-cm$^3$ fractions. Fractions 6 to 13 are combined and concentrated to dryness under reduced pressure (0.27 kPa) at a temperature in the region of 40° C. 1.25 g of ethyl (4S,5R)-3-tert-butoxycarbonyl-2-cyclohexanespiro-4-phenyloxazolidine-5-carboxylate [sic] is thereby obtained in the form of a yellow oil.

1,1-Dimethoxycyclohexane may be prepared by the method described by Lorette et al., J. Org. Chem., 24, 1731, (1959).

The new products of general formula (Ia) possess especially advantageous biological activities.

The new products of general formula (Ia) manifest significant inhibitory activity with respect to abnormal cell proliferation, and possess therapeutic properties that enable patients having pathological conditions associated with an abnormal cell proliferation to be treated. The pathological conditions include the abnormal cell proliferation of malignant or non-malignant cells of various tissues and/or organs comprising, without implied limitation, muscle, bone or connective tissue, the skin, brain, lungs, sex organs, lymphatic or renal systems, mammary or blood cells, liver, digestive system, pancreas and thyroid or adrenal glands. These pathological conditions can also include psoriasis, solid tumors, cancers of the ovary, breast, brain, prostate, colon, stomach, kidney or testicles, Kaposi's sarcoma, cholangiocarcinoma, choriocarcinoma, neuroblastoma, Wilms' tumour, Hodgkin's disease, melanomas, multiple myeloma, chronic lymphocytic leukaemia, and acute or chronic granulocytic lymphoma. The new products according to the invention are especially useful for the treatment of cancer of the ovary. The products according to the invention may be used to prevent or delay the appearance or reappearance of the pathological conditions, or for treating these pathological conditions.

The products according to the invention may be administered to a patient according to different forms suited to the chosen administration route, which is preferably the parenteral route. Parenteral administration comprises intravenous, intraperitoneal, intramuscular or subcutaneous administrations. Intraperitoneal or intravenous administration is more especially preferred.

The present invention also comprises pharmaceutical compositions containing at least one product of general formula (Ia) in a sufficient amount suitable for use in human or veterinary therapy. The compositions may be prepared according to the customary methods, using one or more pharmaceutically acceptable adjuvants, vehicles or excipients. Appropriate vehicles include diluents, sterile aqueous media and various nontoxic solvents. Preferably, the compositions take the form of aqueous solutions or suspensions, injectable solutions which can contain emulsifying agents, colorants, preservatives or stabilizers.

The choice of adjuvants or excipients may be determined by the solubility and chemical properties of the product, the particular mode of administration and good pharmaceutical practice.

For parenteral administration, sterile aqueous or non-aqueous solutions or suspensions are used. For the preparation of non-aqueous solutions or suspensions, natural vegetable oils such as olive oil, sesame oil or liquid paraffin, or injectable organic esters such as ethyl oleate, may be used. The sterile aqueous solutions can consist of a solution of a pharmaceutically acceptable salt dissolved in water. Aqueous solutions are suitable for intravenous administration provided the pH is appropriately adjusted and the solution is made isotonic, for example with a sufficient amount of sodium chloride or glucose. The sterilization [sic] may be carried out by heating or by any other means which does not adversely affect the composition.

It is obvious that all the products participating in the compositions according to the invention must be pure and nontoxic in the amounts used.

The compositions can contain at least 0.01% of therapeutically active product. The amount of active product in the composition is such as to enable an appropriate dosage to be prescribed. Preferably, the compositions are prepared in such a way that a single dose contains from 0.01 to 1,000 mg approximately of active product for parenteral administration.

The therapeutic treatment may be carried out conjointly with other therapeutic treatments including antineoplastic medicinal products, monoclonal antibodies, immunological therapies or radiotherapies or biological-response modifiers. The response modifiers include, without implied limitation, lymphokines and cytokines such as interleukins, interferons ($\alpha$, $\beta$ or $\delta$) and TNF. Other chemotherapeutic agents which are useful in the treatment of disorders due to abnormal cell proliferation include, without implied limitation, alkylating agents such as nitrogen mustards, for instance mechlorethamine, cyclophosphamide, melphalan and chlorambucil, alkyl sulphonates such as busulphan, nitrosoureas such as carmustine, lomusine, semustine and streptozocin, triazenes such as dacarbazine, antimetabolites such as folic acid analogues, for instance methotrexate, pyrimidine analogues such as fluorouracil and cytarabine, purine analogues such as mercaptopurine and thioguanine, natural products such as vinca alkaloids, for instance vinblastine, vincristine and vendesine, epipodophyllotoxins such as etoposide and teniposide, antibiotics such as dactinomycin, daunorubicin, doxorubicin, bleomycin, plicamycin and mitomycin, enzymes such as L-asparaginase, various agents such as coordination complexes of platinum, for example cisplatin, substituted ureas such as hydroxyurea, methylhydrazine derivatives such as procarbazine, adrenocoticoid [sic] suppressants such as mitotane and aminoglutethimide, hormones and antagonists such as adrenocorticosteroids such as prednisone, progestins such as hydroxyprogesterone caproate, methoxyprogesterone acetate and megestrol acetate, oestrogens such as diethylstilboestrol and ethinyloestradiol, antioestrogens such as tamoxifen, and androgens such as testosterone propionate and fluoxymesterone.

The doses used for implementing the methods according to the invention are those which permit a prophylactic treatment or a maximum therapeutic response. The doses vary according to the form of administration, the particular product selected and the features distinctive to the subject to be treated. In general, the doses are those which are therapeutically effective for the treatment of disorders due to an abnormal cell proliferation. The products according to the invention may be administered as often as necessary to obtain the desired therapeutic effect. Some patients may respond rapidly to relatively high or low doses, and then require low or zero maintenance doses. Generally, low doses will be used at the beginning of the treatment and, if necessary, increasingly higher doses will be administered until an optimum effect is obtained. For other patients, it may be necessary to administer maintenance doses 1 to 8 times a day, preferably 1 to 4 times, according to the physiological requirements of the patient in question. For some patients, it is also possible for it to be necessary to use only one to two daily administrations.

In humans, the doses are generally between 0.01 and 200 mg/kg. Intraperitoneally, the doses will generally be between 0.1 and 100 mg/kg, and preferably between 0.5 and 50 mg/kg, and still more specifically between 1 and 10 mg/kg. Intravenously, the doses are generally between 0.1 and 50 mg/kg, and preferably between 0.1 and 5 mg/kg, and still more specifically between 1 and 2 mg/kg. It is understood that, in order to choose the most suitable dosage, account should be taken of the administration route, the patient's weight, general state of health and age and all factors which may influence the efficacy of the treatment.

The example which follows illustrates a composition according to the invention.

EXAMPLE 40 mg of the product obtained in Example 1 are dissolved in 1 cm$^3$ of Emulphor EL 620 and 1 cm$^3$ of ethanol, and the solution is then diluted by adding 18 cm$^3$ of physiological fluid.

The composition is administered by introduction into a perfusion of a physiological solution for 1 hour.

We claim:

1. Process for preparing taxane derivatives of general formula:

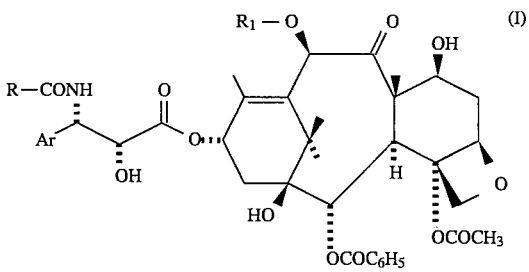

in which R represents a t-butoxy or phenyl radical, $R_1$ represents a hydrogen atom or an acetyl radical and Ar represents an aryl radical, characterized in that:

a) an oxazolidine derivative of general formula:

in which Ar is defined as above, Boc represents a t-butoxycarbonyl radical and $R_6$ and $R_7$, which may be identical or different, represent an alkyl radical containing 1 to 4 carbon atoms, optionally substituted with one or more aryl radicals, or an aryl, or alternatively $R_6$ and $R_7$, together with the carbon atom to which they are linked, form a 4- to 7-membered ring, is condensed with a taxane derivative of general formula:

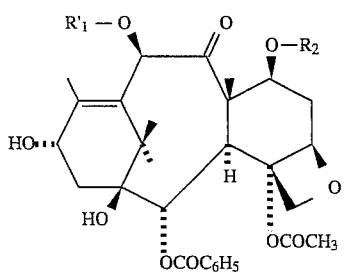

in which R'$_1$ represents an acetyl radical or a group protecting the hydroxyl function and R$_2$ represents a group protecting the hydroxyl function, to obtain a product of general formula:

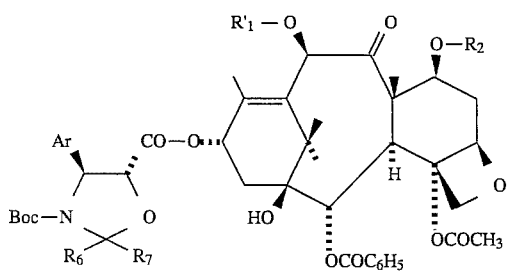

in which Ar, R'$_1$, R$_2$, R$_6$ and R$_7$ are defined as above, b) the product is treated in an acid medium, under conditions which have no effect on R'$_1$ and R$_2$, to obtain the product of general formula:

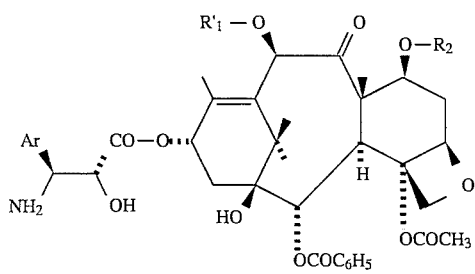

in which R'$_1$ and R$_2$ are defined as above, c) the product is treated with a suitable reagent enabling a t-butoxycarbonyl or benzoyl radical to be introduced on the amino function to obtain a product of general formula:

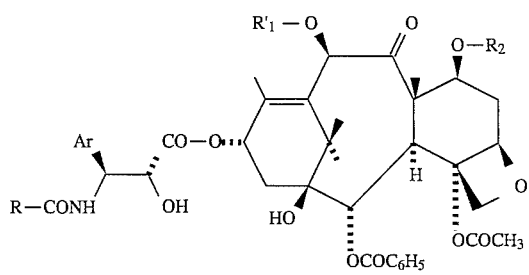

d) the protective groups R'$_1$ and R$_2$ are replaced by hydrogen atoms, and then e) the product obtained is isolated and, purified.

2. Process according to claim 1 for the preparation of a product of general formula (I) in which R and R$_1$ are defined as in claim 1 and Ar represents an optionally substituted phenyl radical or an α- or β-naphthyl radical optionally substituted with one or more atoms or radicals selected from halogen atoms and alkyl, aryl, arylalkyl, alkoxy, alkylthio, aryloxy, arylthio, mercapto, acylamino, aroylamino, alkoxycarbonylamino, amino, alkylamino, dialkylamino, carboxyl, alkoxycarbonyl, carbamoyl, dialkylcarbamoyl, cyano, nitro and trifluoromethyl radicals, on the understanding that the alkyl radicals and the alkyl portions of the other radicals contain 1 to 4 carbon atoms and that the aryl radicals are phenyl or α- or β-naphthyl radicals.

3. Process according to one of claims 1 and 2, characterized in that the protective radicals represented by R'$_1$ and R$_2$ are 2,2,2-trichloroethoxycarbonyl radicals or radicals which can be converted to 2,2,2-trichloroethoxycarbonyl radicals.

4. Process according to one of claims 1 to 3, characterized in that the condensation of the product of general formula (II) with the taxane derivative of general formula (III) is performed in the presence of a condensing agent and an activating agent.

5. Process according to one of claims 1 to 4, characterized in that the selective treatment of the product of general formula (IV) is performed by means of an inorganic or organic acid, where appropriate in an alcohol.

6. Process according to one of claims 1 to 5, characterized in that the introduction of a t-butoxycarbonyl or benzoyl radical into the product of general formula (V) is performed by means of di-t-butyl dicarbonate or benzoyl chloride.

7. Process according to one of claims 1 to 6, characterized in that the replacement of the protective groups represented by R'$_1$ and R$_2$ by hydrogen atoms is performed with zinc in an acetic acid medium or by means of an inorganic or organic acid in an aliphatic alcohol in the presence of zinc.

8. The new taxane derivatives of general formula:

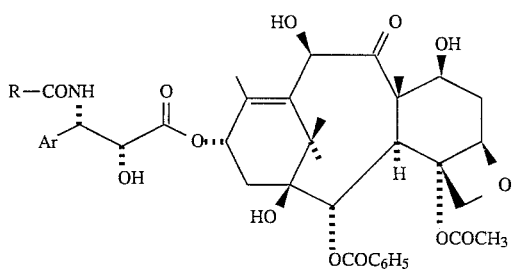

in which R represents a t-butoxy or phenyl radical and Ar represents a substituted phenyl or α- or β-naphthyl radical optionally substituted with one or more atoms or radicals selected from halogen atoms and alkyl, aryl, aralkyl, alkoxy, alkylthio, aryloxy, arylthio, mercapto, acylamino, aroylamino, alkoxycarbonylamino, amino, alkylamino, dialkylamino, carboxyl, alkoxycarbonyl, carbamoyl, dialkylcarbamoyl, cyano, nitro and trifluoromethyl radicals, on the understanding that the alkyl radicals and the alkyl portions of the other radicals contain 1 to 4 carbon atoms and that the aryl radicals are phenyl or α- or β-naphthyl radicals.

9. The process according to claim 1, wherein the aryl radical is phenyl.

10. The process according to claim 2, wherein the halogen atoms are selected from the group comprising fluorine, chlorine, bromine and iodine.

11. The process according to claim 8, wherein the halogen atoms are selected from the group comprising fluorine, chlorine, bromine and iodine.

12. Pharmaceutical composition characterized in that it contains a sufficient amount of at least one derivative according to claim 8, in the pure state or in combination with one or more pharmaceutically acceptable products which can be either inert or physiologically active.

13. The oxazolidine derivatives of general formula:

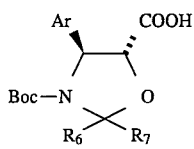

in which Ar is defined according to one of claims 1 and 2, Boc represents a t-butoxycarbonyl radical and $R_6$ and $R_7$, which may be identical or different, represent an alkyl radical containing 1 to 4 carbon atoms, optionally substituted with one or more aryl radicals, or an aryl, or alternatively $R_6$ and $R_7$, together with the carbon atom to which they are linked, form a 4- to 7-membered ring.

14. Process for preparing an oxazolidine derivative according to claim 13, characterized in that a methoxyalkene optionally substituted with one or more aryl radicals, a dimethoxyalkane optionally substituted with one or more aryl radicals or a gemdimethoxycycloalkane containing 4 to 7 carbon atoms is reacted with a phenylisoserine derivative of general formula:

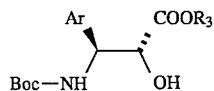

in which Ar is defined according to one of claims 1 and 2, Boc represents a t-butoxycarbonyl radical and R represents an alkyl radical containing 1 to 4 carbon atoms optionally substituted with a phenyl radical, and the product obtained is then saponified.

15. The process according to claim 13, wherein the aryl radical is phenyl.

* * * * *